(12) United States Patent
Reid

(10) Patent No.: US 10,485,582 B2
(45) Date of Patent: Nov. 26, 2019

(54) CANNULAS HAVING BODY WALL RETENTION FEATURES, AND RELATED SYSTEMS AND METHODS

(71) Applicant: Intuitive Surgical Operations, Inc., Sunnyvale, CA (US)

(72) Inventor: Robert C. Reid, Fairfield, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 49 days.

(21) Appl. No.: 15/622,935

(22) Filed: Jun. 14, 2017

(65) Prior Publication Data

US 2018/0021061 A1    Jan. 25, 2018

Related U.S. Application Data

(60) Provisional application No. 62/365,778, filed on Jul. 22, 2016.

(51) Int. Cl.
*A61B 17/34*    (2006.01)
*A61B 17/00*    (2006.01)

(52) U.S. Cl.
CPC ...... *A61B 17/3423* (2013.01); *A61B 17/3421* (2013.01); *A61B 2017/00526* (2013.01); *A61B 2017/3484* (2013.01)

(58) Field of Classification Search
CPC ......... A61B 17/3421–3439; A61B 2017/3433; A61B 2017/348–3492
See application file for complete search history.

(56) References Cited

U.S. PATENT DOCUMENTS

| | | | | |
|---|---|---|---|---|
| 5,403,336 A | * | 4/1995 | Kieturakis | A61B 17/3421 606/164 |
| 5,556,411 A | | 9/1996 | Taoda et al. | |
| 5,634,911 A | * | 6/1997 | Hermann | A61B 17/3417 604/246 |
| 5,697,913 A | | 12/1997 | Sierocuk et al. | |
| 5,716,369 A | * | 2/1998 | Riza | A61B 17/0469 606/139 |

(Continued)

FOREIGN PATENT DOCUMENTS

| | | |
|---|---|---|
| WO | WO-2015142812 A1 | 9/2015 |
| WO | WO-2015142814 A1 | 9/2015 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Eduardo C Robert
*Assistant Examiner* — Michelle C Eckman
(74) *Attorney, Agent, or Firm* — Jones Robb, PLLC

(57) ABSTRACT

A cannula may include a cannula bowl having an opening to receive an instrument configured to be advanced through the cannula, and a cannula tube extending distally from the cannula bowl. The cannula tube may have a proximal end opening, a distal end opening disposed at an opposite end of the cannula from the proximal end opening, and lateral wall defining a passage extending from the proximal end opening to the distal end opening. The lateral wall can have outer dimensions defining a waisted portion with smaller outer dimensions than a region disposed proximally or distally to the waisted portion along a length of the cannula tube.

19 Claims, 20 Drawing Sheets

(56) References Cited

U.S. PATENT DOCUMENTS

| | | | |
|---|---|---|---|
| 5,746,720 A * | 5/1998 | Stouder, Jr. | A61B 17/3417 604/117 |
| 5,895,351 A * | 4/1999 | Nottage | A61B 17/3421 600/201 |
| 5,993,471 A * | 11/1999 | Riza | A61B 17/3498 606/185 |
| 5,997,515 A * | 12/1999 | de la Torre | A61B 17/3417 604/246 |
| 7,316,699 B2 | 1/2008 | McFarlane | |
| 8,888,692 B1 * | 11/2014 | Pravongviengkham | A61B 17/3417 600/207 |
| 9,668,723 B2 * | 6/2017 | Keating | A61B 17/3423 |
| 9,808,282 B2 * | 11/2017 | Spenciner | A61B 17/3421 |
| 10,201,346 B2 * | 2/2019 | Malkowski | A61M 5/329 |
| 2004/0006344 A1 * | 1/2004 | Nguyen | A61B 17/3431 606/191 |
| 2005/0059934 A1 * | 3/2005 | Wenchell | A61B 17/3439 604/167.01 |
| 2005/0070949 A1 * | 3/2005 | Bakos | A61B 1/00154 606/191 |
| 2005/0096507 A1 * | 5/2005 | Prosek | A61B 17/34 600/204 |
| 2005/0209607 A1 * | 9/2005 | Lipchitz | A61B 17/3421 606/108 |
| 2006/0111739 A1 * | 5/2006 | Staufer | A61B 17/00234 606/192 |
| 2006/0142779 A1 * | 6/2006 | Arramon | A61B 17/3421 606/92 |
| 2006/0211992 A1 * | 9/2006 | Prosek | A61B 17/3498 604/167.06 |
| 2006/0212061 A1 * | 9/2006 | Wenchell | A61B 17/3421 606/191 |
| 2006/0217665 A1 * | 9/2006 | Prosek | A61B 17/3421 604/167.02 |
| 2007/0088258 A1 * | 4/2007 | Wenchell | A61B 17/34 604/104 |
| 2007/0088277 A1 * | 4/2007 | McGinley | A61B 17/3462 604/167.01 |
| 2007/0239108 A1 * | 10/2007 | Albrecht | A61B 17/3415 604/96.01 |
| 2008/0097332 A1 * | 4/2008 | Greenhalgh | A61B 17/3421 604/167.06 |
| 2008/0208131 A1 * | 8/2008 | Powers | A61B 17/3421 604/164.11 |
| 2009/0182282 A1 * | 7/2009 | Okihisa | A61B 17/3421 604/165.01 |
| 2010/0036307 A1 * | 2/2010 | Von Segesser | A61B 17/3439 604/6.16 |
| 2010/0076478 A1 * | 3/2010 | Smith | A61B 17/3417 606/185 |
| 2010/0100045 A1 * | 4/2010 | Pravongviengkham | A61B 17/3421 604/164.09 |
| 2010/0262166 A1 * | 10/2010 | Boraiah | A61B 17/0057 606/148 |
| 2010/0268024 A1 * | 10/2010 | Brannon | A61B 1/00154 600/104 |
| 2010/0268164 A1 * | 10/2010 | Chung | A61B 17/3421 604/167.03 |
| 2011/0028796 A1 * | 2/2011 | Blinman | A61B 17/3421 600/227 |
| 2011/0040149 A1 * | 2/2011 | Smith | A61B 1/3132 600/114 |
| 2011/0087167 A1 * | 4/2011 | Albrecht | A61B 17/3421 604/164.04 |
| 2011/0144440 A1 * | 6/2011 | Cropper | A61B 17/3421 600/203 |
| 2011/0144442 A1 * | 6/2011 | Farrell | A61B 1/32 600/206 |
| 2011/0144448 A1 * | 6/2011 | Shelton, IV | A61B 17/3423 600/216 |
| 2011/0152773 A1 * | 6/2011 | McCawley | A61B 17/3421 604/164.01 |
| 2011/0306841 A1 * | 12/2011 | Lozman | A61B 17/1684 600/204 |
| 2012/0010569 A1 * | 1/2012 | Parihar | A61B 17/3421 604/167.01 |
| 2012/0123216 A1 * | 5/2012 | Winfree | A61B 1/00071 600/208 |
| 2012/0289816 A1 * | 11/2012 | Mark | A61M 39/0247 600/411 |
| 2012/0310147 A1 * | 12/2012 | Poll | A61B 17/3417 604/24 |
| 2012/0323081 A1 * | 12/2012 | Son | A61M 39/0247 600/215 |
| 2013/0116510 A1 * | 5/2013 | Lutze | A61B 1/32 600/208 |
| 2013/0197439 A1 * | 8/2013 | Melvin | A61B 17/3417 604/117 |
| 2013/0325031 A1 | 12/2013 | Schena et al. | |
| 2013/0325033 A1 | 12/2013 | Schena et al. | |
| 2013/0338435 A1 * | 12/2013 | Shen | A61B 17/3417 600/106 |
| 2014/0163323 A1 * | 6/2014 | Mohajer-Shojaee | A61B 17/0057 600/204 |
| 2014/0187922 A1 * | 7/2014 | Mark | A61B 5/064 600/424 |
| 2014/0206942 A1 * | 7/2014 | Webb | A61B 17/3421 600/208 |
| 2014/0207084 A1 * | 7/2014 | Webb | A61M 39/0247 604/264 |
| 2014/0249371 A1 * | 9/2014 | Fischvogt | A61B 17/3417 600/114 |
| 2014/0257356 A1 * | 9/2014 | Pacak | A61B 17/3417 606/185 |
| 2014/0364697 A1 * | 12/2014 | Son | A61B 1/32 600/215 |
| 2015/0065808 A1 * | 3/2015 | Van Wyk | A61B 17/3462 600/208 |
| 2015/0094751 A1 * | 4/2015 | Chen | A61B 17/34 606/185 |
| 2015/0123355 A1 | 5/2015 | Castro et al. | |
| 2015/0164547 A1 * | 6/2015 | Sauter | A61B 17/3421 600/204 |
| 2015/0216514 A1 * | 8/2015 | Weisbrod | A61B 17/0401 606/232 |
| 2015/0272617 A1 * | 10/2015 | MacDonald | A61B 1/05 600/110 |
| 2016/0045224 A1 * | 2/2016 | Hendershot, III | A61B 17/3474 604/26 |
| 2016/0106461 A1 * | 4/2016 | Morris | A61B 17/3421 600/204 |
| 2016/0158005 A1 * | 6/2016 | Wells | A61B 17/3417 604/167.03 |
| 2016/0220271 A1 * | 8/2016 | Mastri | A61B 17/0218 |
| 2017/0007296 A1 * | 1/2017 | Dannaher | A61B 17/34 |
| 2017/0209134 A1 * | 7/2017 | Wagner | A61B 17/0218 |
| 2017/0245888 A1 * | 8/2017 | Buyda | A61B 17/00234 |
| 2017/0281229 A1 * | 10/2017 | Hess | A61B 17/0218 |
| 2018/0132890 A1 * | 5/2018 | Morrissette | A61B 17/3421 |
| 2018/0214177 A1 * | 8/2018 | Chen | A61B 17/0218 |
| 2018/0256019 A1 * | 9/2018 | Rosenbaum | A61B 1/126 |
| 2018/0310958 A1 * | 11/2018 | Silver | A61B 17/3423 |
| 2019/0038313 A1 * | 2/2019 | Hendershot, III | A61B 17/3474 |

* cited by examiner

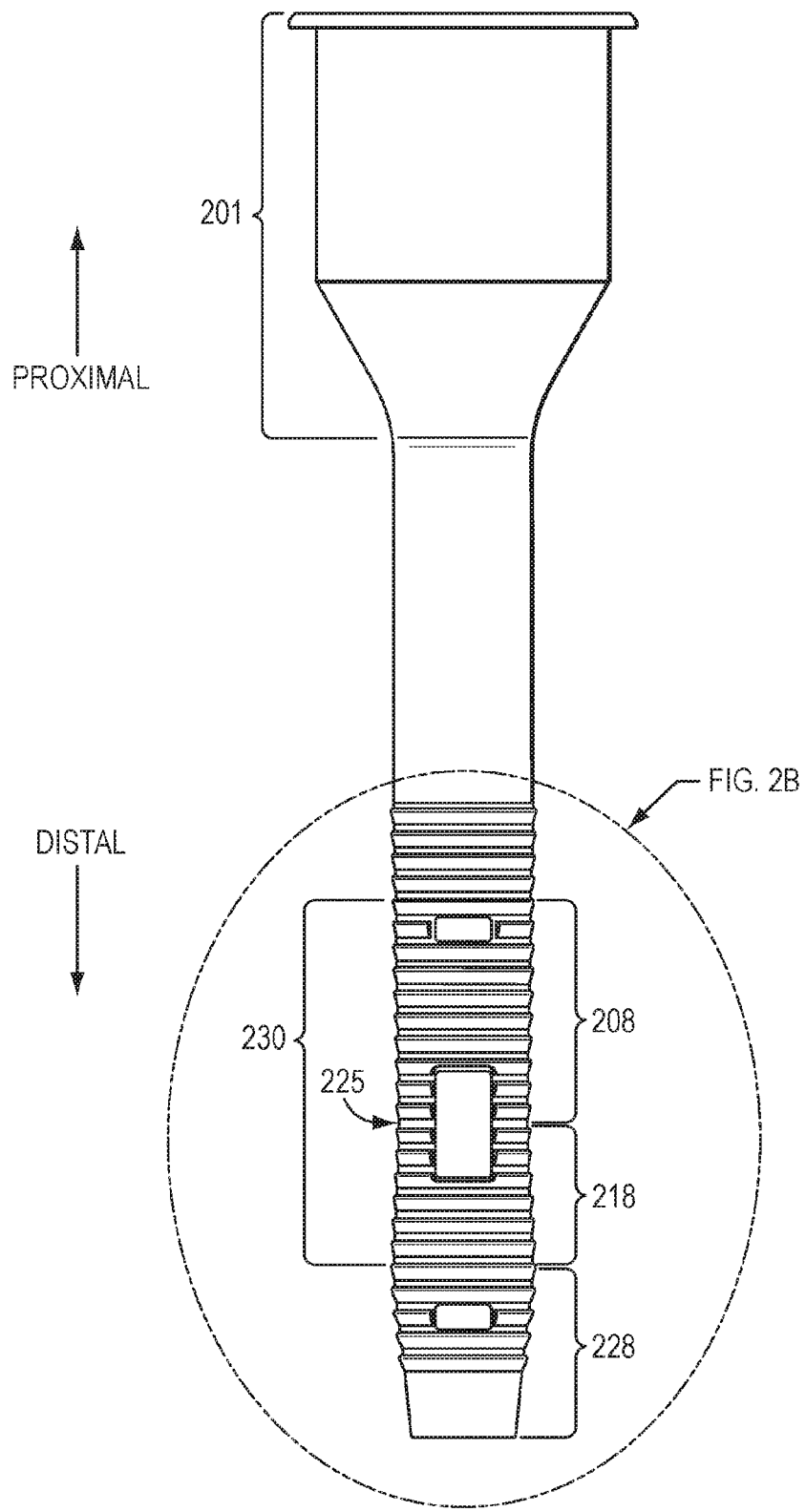

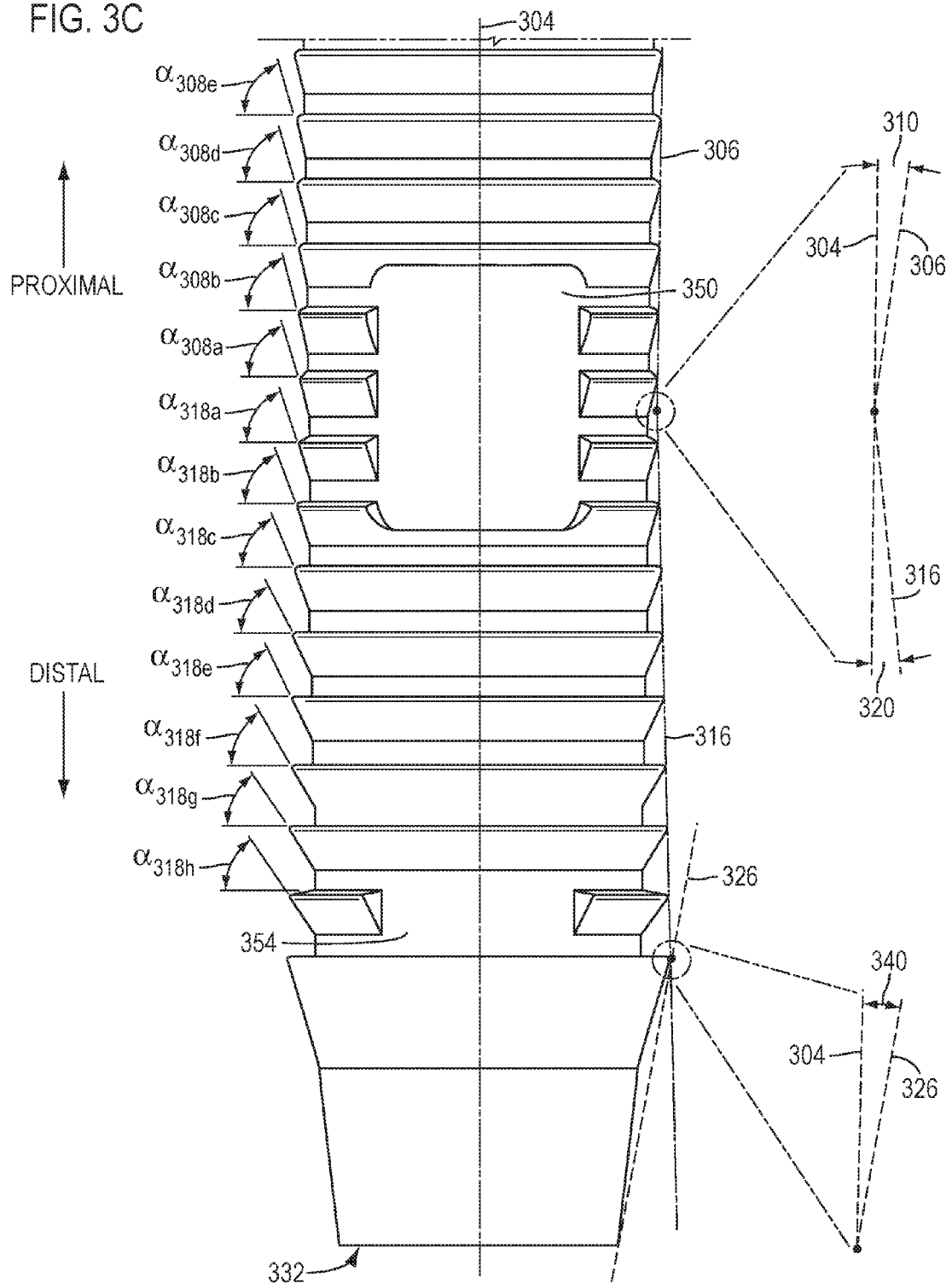

CANNULAS HAVING BODY WALL RETENTION FEATURES, AND RELATED SYSTEMS AND METHODS

CROSS-REFERENCE TO RELATED APPLICATIONS

This application claims priority to U.S. Provisional Application No. 62/365,778, filed Jul. 22, 2016, which is incorporated by reference herein in its entirety.

TECHNICAL FIELD

The present disclosure relates generally to cannulas used in laparoscopic surgery, and related systems and methods. More specifically, the present disclosure relates to a cannula body with retention features configured to retain a position of the cannula relative to a body wall into which the cannula is inserted.

INTRODUCTION

Remotely controlled surgical instruments, including surgical instruments operated at least in part with computer assistance, such as instruments operated with robotic "master-slave" and other remote telepresence technology, are often used in minimally invasive medical procedures. In teleoperated, computer-assisted surgical systems, surgeons manipulate input devices at a surgeon console, and those "master" inputs are passed to a patient side cart that interfaces with one or more remotely controlled surgical instruments coupled to the patient side cart. Based on the surgeon inputs at the surgeon console, the one or more remotely controlled surgical instruments are actuated at the patient side cart to operate on the patient, thereby creating a master-slave control relationship between the surgeon console and the surgical instrument(s) at the patient side cart.

Various minimally invasive procedures, whether performed manually or via robotic, computer-assisted systems, utilize cannulas that are inserted through a port, incision, or opening in a body wall (e.g., a patient's body wall). Surgical instruments are then introduced through the cannula to provide access to a remote surgical or treatment site within the body. In procedures relying on insufflation gas pressure above ambient pressure, cannulas generally include sealing elements to seal against the instruments being inserted through the inlet opening of the cannula, and to also seal against the body wall around an outer lateral surface of the cannula. To provide stability and reduce trauma to the body wall though which a cannula is inserted, it is desirable that the cannula remain relatively stationary once inserted.

In various manual laparoscopic and robotic, computer-assisted surgeries in which the remote center of motion of movement of surgical instruments is generally stationary in space, the cannula generally stays in place with reference to the body wall of the patient. Advances in computer-assisted surgery have facilitated an increased ability to change the location of the remote center of motion in space during a surgical procedure. However, this may lead to an increase in insertion and withdrawal forces acting on a cannula. Such forces have the potential to cause full or partial cannula withdrawal relative to the body during surgery. This could result in an insufflation loss effect, instability during the surgical procedure, and/or trauma to the body wall. Therefore, it may be desirable to provide a cannula with improved retention performance such that the cannula can be held more securely and substantially stationary relative to the body wall during surgery.

SUMMARY

Exemplary embodiments of cannulas and methods of making or using the same, as disclosed herein, may solve one or more of the above-mentioned problems and/or may demonstrate one or more of the above-mentioned desirable features. Other features and/or advantages may become apparent from the description that follows.

In accordance with various exemplary embodiments of the present disclosure, a cannula bowl having an opening to receive an instrument configured to be advanced through the cannula, and a cannula tube extending distally from the cannula bowl. The cannula tube has a proximal end opening, a distal end opening disposed at an opposite end of the cannula from the proximal end opening, and a lateral wall defining a passage extending from the proximal end opening to the distal end opening. The lateral wall can have outer dimensions defining a waisted portion with smaller outer dimensions than a region disposed proximally or distally to the waisted portion along a length of the cannula tube.

In accordance with another exemplary embodiment of the present disclosure, a method of making a cannula can include the step of configuring outer dimensions of the cannula to create a waisted portion along a portion of the cannula between a proximal end and a distal end of the cannula, wherein the proximal end is configured to receive a surgical instrument to be advanced through the cannula toward the distal end. The method of making a cannula can further include of configuring at least one region of the cannula extending proximally or distally from the waisted portion to have larger outer dimensions than the waisted portion.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

FIG. 2A is a side view of an exemplary embodiment of a cannula in accordance with the present disclosure.

FIG. 3C is a detailed side view of the portion labeled FIG. 3C of the cannula of FIG. 3A.

Figure 1:
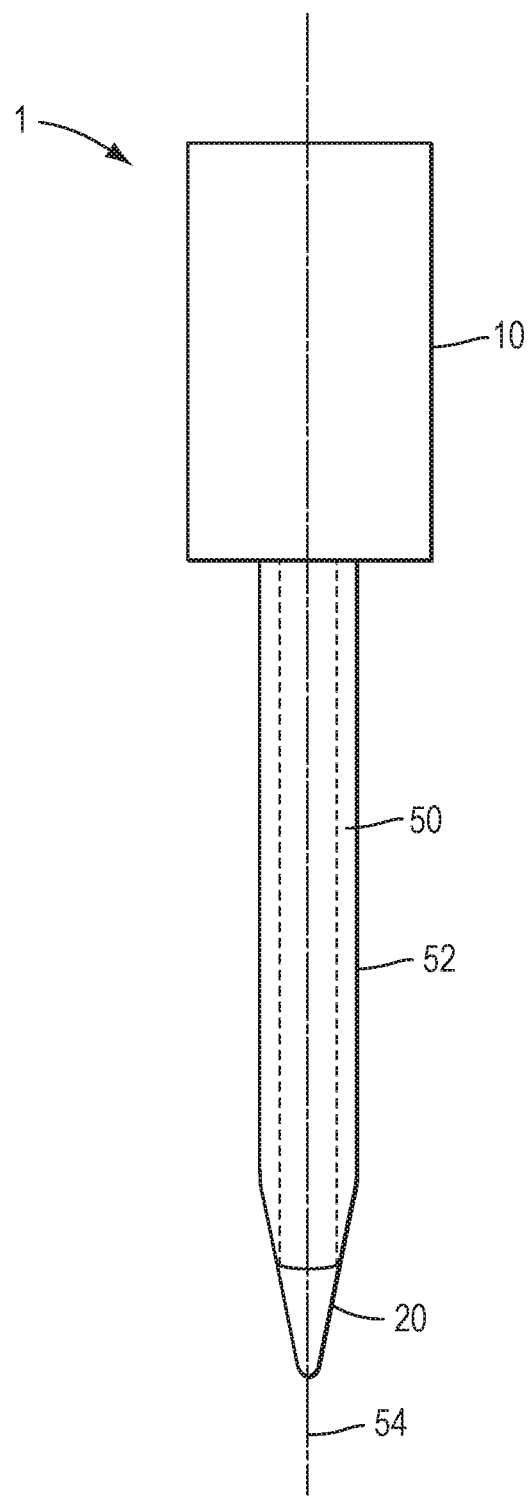
FIG. 1 is a perspective view of a trocar apparatus inserted through a cannula.

Although the following detailed description makes reference to exemplary illustrative embodiments, many alternatives, modifications, and variations thereof will be apparent to those skilled in the art and are contemplated as within the scope of the present disclosure and claims. Accordingly, it is intended that the claimed subject matter is provided its full breadth of scope and to encompass equivalents.

DESCRIPTION OF EXEMPLARY EMBODIMENTS

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

This description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

The present disclosure contemplates cannulas, and related systems and methods, with one or more body wall retention features. Cannulas in accordance with various exemplary embodiments of the present disclosure are designed based in part on, for example, a variety of parameters that can be varied to achieve enhanced retention of a cannula in its inserted position through a body wall of a patient, while also allowing design flexibility to meet a range of applications. Such enhanced retention is desirable, for example, in applications in which the remote center of motion of the cannula may change during a procedure. For example, the use of table motion and/or the use of a software-defined remote center of motion manipulation arm holding a cannula, may result in a change of the location of the remote center of motion in space, which may cause increased insertion and withdrawal forces on the cannula.

In accordance with the present disclosure, the structural configurations of the cannulas disclosed herein provide cannulas with increased retention forces relative to the body wall.

To enhance retention relative to the body wall, various exemplary embodiments of cannulas include a variation in the outer lateral dimension (e.g., diameter) along a length (e.g., axial direction) of the cannula. For example, a cannula may include a flared outer surface region relative to other portions along a length of the cannula. Such a flared region may act as a stop to inhibit the body wall from moving past the flared region in response to a force tending to move the cannula in the axial direction relative to the body wall. Although a flared region may be provided in various locations along the cannula, in one exemplary embodiment a flared region may be located at a region of the cannula distal to a region along a length of the cannula intended to be in contact with the body wall in the inserted position. A flared region could alternatively, or in addition to, be provided proximal to the body wall contact region of the cannula. As illustrated in the figures, a distal direction of the cannula is in a direction toward the end that is intended to be inserted into a patient during a procedure, and a proximal direction is toward the end of the cannula into which an instrument or other material is configured to be introduced for advancement through the cannula.

In various additional exemplary embodiments, to provide increased retention forces, cannulas may include a "waisted" configuration on a portion of the cannula. For example, a portion of an outer surface may be provided with concavity such that portions above and below the concave portion act as shoulders or protruding profiles that inhibit the body wall from moving past them. The cannula may be inserted such that the body wall of the patient sits along the "waisted" region of the cannula. The concave region of the outer surface of the cannula thus has an inflection point or zone and provides a region of smaller outer dimensions (e.g., diameter) relative to other regions of the cannula, in particular regions distally and/or proximally adjacent to the inflection point or zone. In some embodiments, the inflection point or zone optionally defines a discontinuity in the shape (e.g., curvature) of the concave region of the cannula.

Cannulas having such waisted portions in accordance with various exemplary embodiments, may facilitate accurate positioning of the cannula such that a remote center of motion is disposed at a patient's body wall when the cannula is inserted through an incision or other opening in the patient. The positioning may be assisted by the patient's body wall/tissue initially expanding over the regions distal to the waisted zone and then "snapping" back once the cannula is advanced so that the waisted portion is positioned at the body wall. This tactile and/or audible sensation can facilitate surgical personnel in recognizing the cannula is inserted with its center of motion, which is generally located at the waisted portion, positioned at the body wall.

Cannulas in accordance with the present disclosure can be made of, for example, polycarbonate, other thermoplastic polymers or fiber reinforced plastics, stainless steel or other metals, and/or other suitable materials. In various exemplary embodiments, relatively rigid materials that can withstand the torsional forces applied to the cannula though a body wall or other anatomy may be used to make the cannula, though cannulas made from less rigid, relatively compliant materials also are within the scope of the present disclosure. Those of ordinary skill in the art would understand, for example, that the material used for a cannula may be chosen based at least in part on intended application, strength/ weight considerations, cost, overhead surgical space, incision size, and/or other design factors. Furthermore, cannulas in accordance with the present disclosure can be made using various welding, molding (e.g., metal injection molding, plastic injection molding, etc.), solvent bonding, casting techniques, or combinations thereof.

Various exemplary embodiments of cannulas in accordance with the present disclosure also utilize rib features on at least a portion of the outer surface. When such ribs are employed, the ribs may be configured to provide the waisted and/or flared profiles of the cannula.

FIG. 1 schematically illustrates an exemplary embodiment of a surgical instrument apparatus 1 that can be used in various laparoscopic or minimally invasive surgical procedures. A surgical instrument 20 having a force transmission actuation housing 10 at its proximal end is inserted through a cannula 50. In various exemplary embodiments, although hidden from view in FIG. 1, cannula 50 may have a proximal bowl (e.g., bowl portion 201 at FIG. 2A) that initially receives the surgical instrument shaft. Cannulas free of a bowl portion are also contemplated.

In some conventional configurations, cannula 50 has a substantially cylindrical outer lateral wall surface 52 that is substantially longitudinally parallel to the longitudinal axis 54 of the cannula 50 such that the outer diameter of the cannula 50 is substantially uniform along its entire length. Being tubular, cannula 50 also has an inner lateral wall surface, hidden from view in FIG. 1. The inner lateral wall surface is substantially cylindrical, or of other uniform cross-section shape, and substantially longitudinally parallel to the axial direction of the cannula 50 such that the inner diameter of the cannula 50 is substantially uniform along its entire length. In this way, a lumen-like passage is provided within the cannula through which surgical instruments and other objects can be advanced. Alternatively, the outer lateral wall surface 52 and/or the inner lateral wall surface may be slightly tapered to provide a generally frustoconical outer shape to the cannula or at least a portion thereof, for example including the distal end, in particular to enable manufacture by molding techniques and/or promote insertion of the cannula through an incision or other opening in the body wall. The wall of the cannula having lateral inner and outer wall surfaces may have a relatively small thickness as compared to the inner hollow passage surrounded by the lateral inner wall surface.

Figure 11:
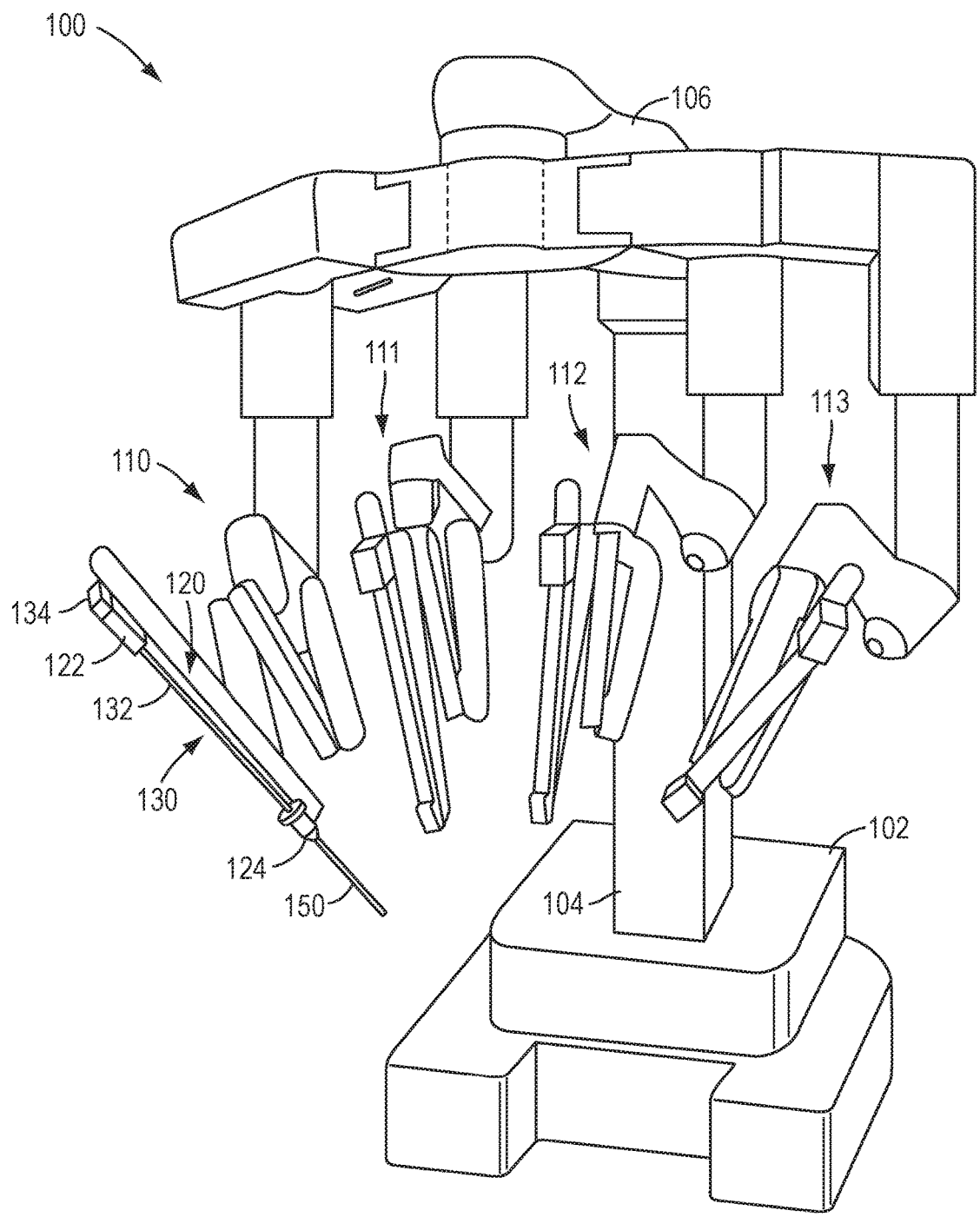
FIG. 11 is a perspective diagrammatic view of a patient side cart in accordance with an exemplary embodiment.

As discussed above, in accordance with various exemplary embodiments, cannulas and surgical instruments of the present disclosure are configured for use in teleoperated, computer-assisted surgical systems. Referring now to FIG. 11, an exemplary embodiment of a patient side cart 100 of a teleoperated, computer-assisted surgical system, to which cannulas and surgical instruments are configured to be mounted for use, is shown. Such a surgical system may further include a surgeon console (not shown) for receiving input from a user to control instruments of patient side cart 100, as well as an auxiliary control/vision cart (not shown), as described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. Non-limiting, exemplary embodiments of teleoperated, computer-assisted surgical systems with which the principles of the present disclosure may be utilized include the da Vinci® Si Surgical System, Single Site da Vinci®

Surgical System, or a da Vinci® Xi Surgical System, available from Intuitive Surgical, Inc. of Sunnyvale, Calif.

Patient side cart 100 includes a base 102, a main column 104, and a main boom 106 connected to main column 104. Patient side cart 100 also includes a plurality of arms 110, 111, 112, 113, which are each connected to main boom 106. Arms 110, 111, 112, 113 each include an instrument mount portion 120 to which an instrument 130 may be mounted, which is illustrated as being attached to arm 110. Portions of arms 110, 111, 112, 113 may be manipulated during a surgical procedure according to commands provided by a user at the surgeon console. In an exemplary embodiment, signal(s) or input(s) transmitted from a surgeon console are transmitted to the control/vision cart, which may interpret the input(s) and generate command(s) or output(s) to be transmitted to the patient side cart 100 to cause manipulation of an instrument 130 (only one such instrument being mounted in FIG. 1) and/or portions of arm 110 to which the instrument 130 is coupled at the patient side cart 100.

Instrument mount portion 120 comprises an actuation interface assembly 122 and a cannula mount 124, with a force transmission mechanism 134 of instrument connecting with the actuation interface assembly 122, according to an exemplary embodiment. Cannula mount 124 is configured to hold a cannula 150 through which shaft 132 of instrument 130 may extend to a surgery site during a surgical procedure. Actuation interface assembly 122 contains a variety of drive and other mechanisms that are controlled to respond to input commands at the surgeon console and transmit forces to the force transmission mechanism 134 to actuate instrument 130, as those skilled in the art are familiar with.

Although the exemplary embodiment of FIG. 11 shows an instrument 130 and cannula 150 attached to only arm 110 for ease of viewing, an instrument and cannula may be attached to any and each of arms 110, 111, 112, 113. An instrument 130 may be a surgical instrument with an end effector or may be an endoscopic imaging instrument or other sensing instrument utilized during a surgical procedure to provide information, (e.g., visualization, electrophysiological activity, pressure, fluid flow, and/or other sensed data) of a remote surgical site. A surgical instrument with an end effector or an imaging instrument may be attached to and used with any of arms 110, 111, 112, 113. However, the embodiments described herein are not limited to the exemplary embodiment of FIG. 11 and various other teleoperated, computer-assisted surgical system configurations may be used with the exemplary embodiments described herein.

It is contemplated that the present disclosure can be applied to various cannula configurations, including, but not limited to, for example, cannula configurations disclosed in International Application Pub. No. WO 2015/142812 A1, entitled "SURGICAL CANNULAS AND RELATED SYSTEMS AND METHODS OF IDENTIFYING SURGICAL CANNULAS" and published Sep. 24, 2015, and International Application Pub. No. WO 2015/142814 A1, entitled "SURGICAL CANNULA MOUNTS AND RELATED SYSTEMS AND METHODS" and published Sep. 24, 2015, each of which is hereby incorporated by reference in its entirety.

Figure 2B:
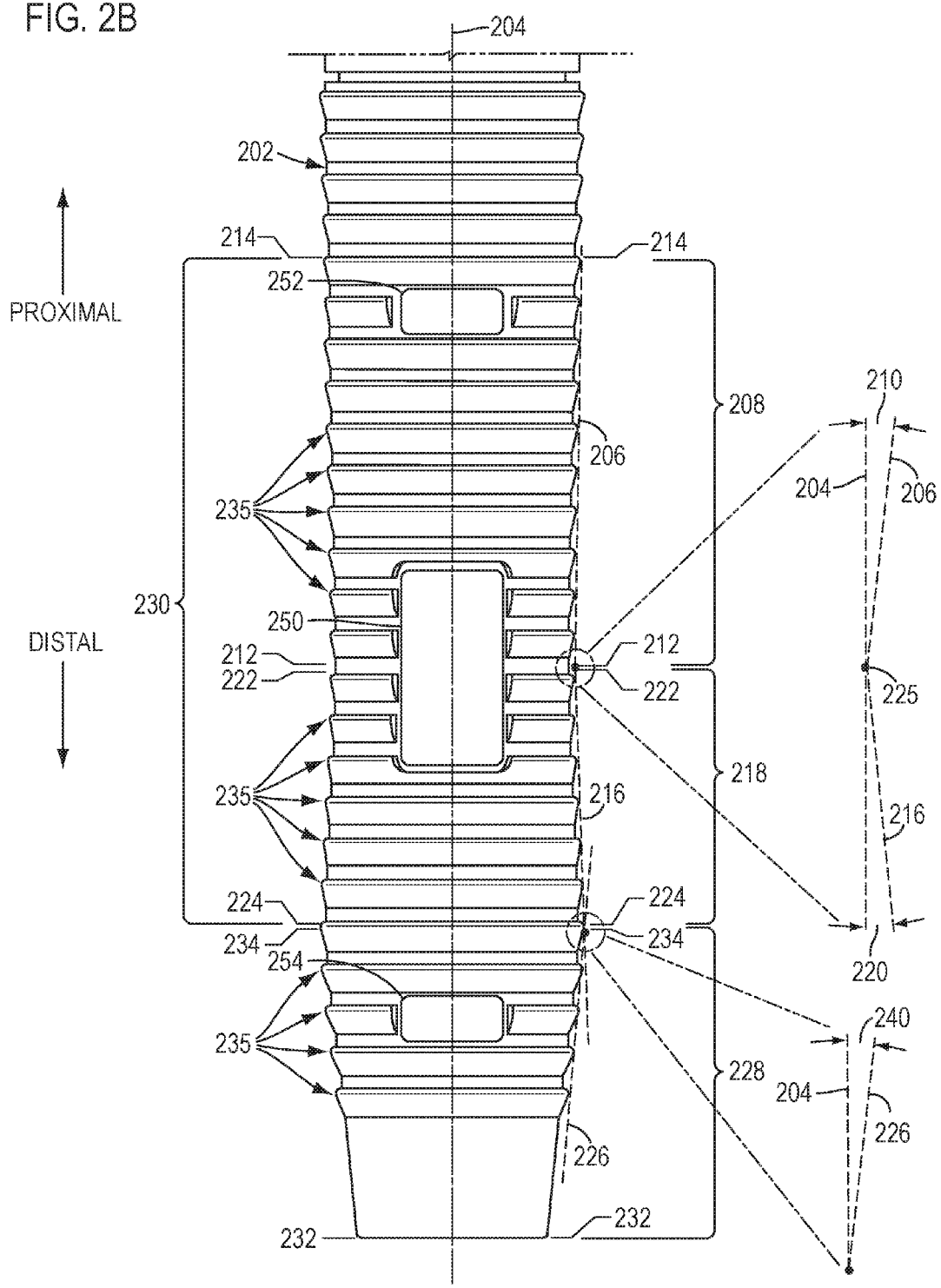
FIG. 2B is a detailed side view of the portion labeled FIG. 2B of the cannula of FIG. 2A.

With reference to FIGS. 2A and 2B, an exemplary embodiment of cannula 200 with enhanced retention features in accordance with the present disclosure is illustrated. Cannula 200 has a lateral inner wall surface (hidden from view), that may be cylindrical or slightly tapered, in whole or in part, to enable manufacture by molding techniques, as described above. The outer lateral wall surface has a configuration that enhances retention of the cannula 200 relative to a body wall in an inserted position. Cannula 200 has outer lateral dimensions that provide a waisted portion 230. The waisted portion 230 includes a first tapered portion 208 (also called first tapered region 208) and a second tapered portion 218 (also called second tapered region 218). A first taper 206 defines the lateral (e.g., radial) outer limits of a first tapered portion 208 of cannula 200. The first taper 206 has a first taper angle 210 that can be measured relative to a longitudinal axis 204 of the cannula 200. First tapered portion 208 has a first tapered portion narrow end 212 and a first tapered portion wide end 214.

Various first taper angle 210 sizes are contemplated. For example, the size of the first taper angle 210 may range from about 1° to about 5°. The longitudinal length of the first tapered region 208 (i.e., the length of the first tapered region extending from the first tapered portion narrow end 212 and a first tapered portion wide end 214) may be considered when sizing the first taper angle 210. For example, when the longitudinal length of the first tapered region 208 is relatively large (e.g., about 50 to about 100 millimeters in length), the size of the first taper angle 210 may range from about 1° to about 2°. Alternatively, for example, when the longitudinal length of the first tapered region 208 is relatively small (e.g., about 20 to about 50 millimeters in length), the size of the first taper angle 210 may range from about 2° to about 3°. In some embodiments, the size of the first taper angle 210 is about 1°.

Additionally, the lateral outer dimensions of cannula 200 include a second taper 216 that defines the lateral (e.g., radial) outer limits of the second tapered portion 218. The second taper 216 of cannula 200 has a second taper angle 220 is measured relative to the longitudinal axis 204 of the cannula 200. Second tapered portion 218 has a second tapered portion narrow end 222 and a second tapered portion wide end 224.

Various second taper angle 220 sizes are contemplated. For example, the size of the second taper angle 220 may range from about −1° to about −5°. The longitudinal length of the second tapered region 218 (i.e., the length of the second tapered region extending from the second tapered portion narrow end 222 to the second tapered portion wide end 224) may be considered when sizing the second taper angle 220. For example, when the longitudinal length of the second tapered region 218 is relatively large (e.g., about 20 to 40 millimeters in length), the size of the second taper angle 220 may range from about −1° to about −2°. Alternatively, for example, when the longitudinal length of the second tapered region 218 is relatively small (e.g., about 5 to 20 millimeters in length), the size of the second taper angle 220 may range from about −2° to about −3°. In some embodiments, the size of the second taper angle 220 is about −1°.

Figure 4:
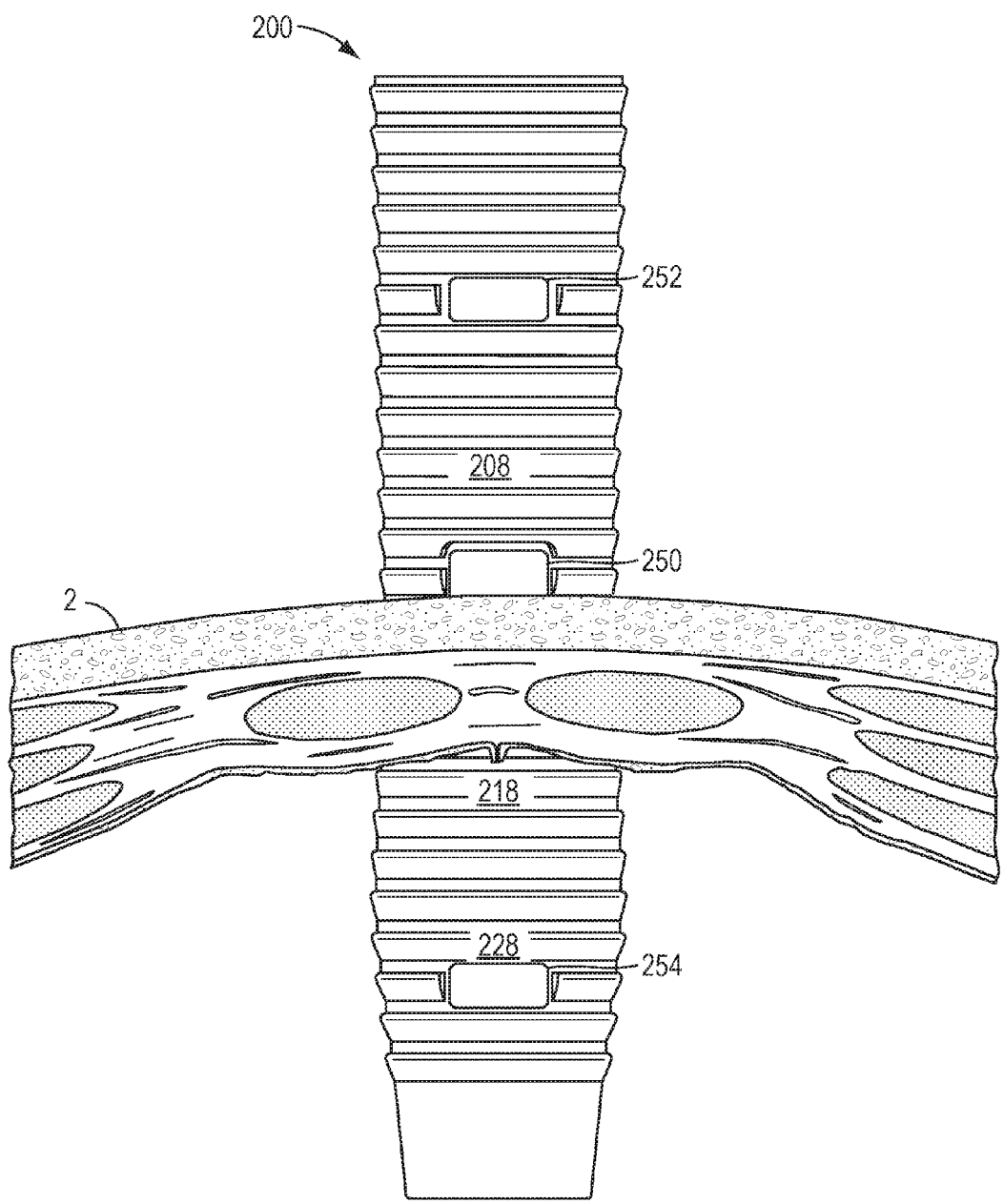
FIG. 4 is a detailed side view of the cannula of FIG. 2A in an inserted position relative to a body wall of a patient.

The narrow end 212 of the first tapered portion 208 can be adjacent to but slightly axially spaced from the narrow end 222 of the second tapered portion 218, although it is also contemplated that they could be at approximately the same axial position. The first tapered portion 208 and the second tapered portion 218 can be integral or distinct components. The juncture where the narrow ends 212 and 222 meet defines an inflection location 225 of the waisted portion 230 of the cannula 200. In this exemplary embodiment, the remote center of the cannula 200 is disposed about the inflection location 225. FIG. 4 shows that the cannula 200 may be inserted within a patient such that the body wall 2 is disposed to surround a region of the cannula 200 including the inflection location 225 (hidden from view in FIG. 4) of the cannula 200.

As further depicted in FIGS. 2A and 2B, the outer lateral dimensions of cannula 200 also optionally includes a third taper 226 that defines the lateral (e.g., radial) outer limits of a third tapered portion 228. The third tapered portion 228 includes a distal end of the cannula 200, with proximal and distal directions labeled in FIGS. 2A and 2B. The third taper 226 has a third taper angle 240 that can be measured relative to the longitudinal axis 204 of the cannula 200. Third tapered portion 228 has a third tapered portion narrow end 232 and a third tapered portion wide end 234.

Various third taper angle 240 sizes are contemplated. For example, the size of the third taper angle 240 may range from about 1° to about 5°. The longitudinal length of the third tapered region 228 (i.e., the length of the third tapered region 228 extending from the third tapered portion narrow end 232 and a third tapered portion wide end 234) may be considered when sizing the third taper angle 240. For example, when the longitudinal length of the third tapered region 228 is relatively large (e.g., about 20 to 50 millimeters in length), the size of the third taper angle 240 may range from about 1° to about 2°. Alternatively, for example, when the longitudinal length of the third tapered region 228 is relatively small (e.g., about 5 to about 20 millimeters in length), the size of the third taper angle 240 may range from about 2° to about 3°. In some embodiments, the size of the third taper angle 240 is about 2°.

In various embodiments, the magnitude of the size of the first taper angle 210 and the magnitude the size of the second taper angle 220 may be about the same. Further, in some embodiments, the magnitude of the size of the third taper angle 240 may be relatively larger than the magnitude of the size of the first taper angle 210 and/or the magnitude the size of the second taper angle 220. Thus, in various exemplary embodiments, the size of the first taper angle 210 is from about 1° to about 2°, the size of the second taper angle 220 is from about −1° to about −2°, and the size of the third taper angle 240 is from about 2° to about 3°. Accordingly, in an exemplary embodiment, the size of the first taper angle 210 is about 1°, the size of the second taper angle 220 is about −1°, and the size of the third taper angle 240 is about 2°.

The wide end 224 of the second tapered portion 218 may be collocated or adjacent but slightly axially spaced from the wide end 234 of the third tapered portion 228. The second tapered portion 218 and the third tapered portion 228 of cannula 200 may be integral or distinct components.

In an alternative embodiment, it is envisioned as within the scope of the present disclosure that instead of having the third taper 226, the cannula 200 can have outer lateral dimensions such that the cannula outer surface extends straight from wide end 224 of the second tapered portion 218 to the distal end of the cannula 200 (i.e., the taper angle 240 may be about 0°).

As shown in FIG. 2B, the waisted portion 230 thus may extend from a waist proximal end at first tapered portion wide end 214 to a waist distal end at the second tapered portion wide end 224. Further, the end 232 is the distal end of the cannula 300. A cannula according to the present disclosure can further include additional portions that extend proximally from wide end 214 and/or distally from the wide end 224 such that the proximal end of the cannula 200 is beyond wide end 214 and/or the distal end of the cannula 200 is beyond the wide end 224.

Cannula 200 also includes radially protruding ribs 235 extending from the outer lateral wall surface 202. Ribs 235 may be distinct from or integrally formed with the outer lateral wall surface 202. In FIGS. 2A and 2B, the ribs 235 are uniformly spaced apart in the axial direction. Alternatively, the ribs 235 of a cannula in accordance with the present disclosure can be non-uniformly spaced. In other words, the space between adjacent ribs can be varied with respect to the space between other adjacent ribs. The total number of ribs 235 on the cannula 200 also can vary. Also, the number of ribs 235 within each tapered portion 208, 218, and 228 can vary. Along a longitudinal cross-sectional plane of the cannula 200, the outer lateral wall surface 202 may be parallel to each taper 206, 216, and 226, such that the outer lateral wall surface 202 along a longitudinal cross-sectional plane of the cannula 200 has the same taper angle relative to the longitudinal axis 204 as the angle of the tapered portions 208, 218, and 228, respectively. Moreover, as shown in the figures, in various exemplary embodiments that include ribs, it is contemplated that a distal end portion be free of ribs so as to facilitate a smooth insertion of the cannula into an incision or other opening in the body wall. Further, as shown in FIG. 2A, in an exemplary embodiment, the cannula 200 can be free of ribs along a portion of the cannula tube extending from the cannula bowl portion 201 to a location proximal or starting at the proximal end of the waisted portion 230.

Figure 5A:
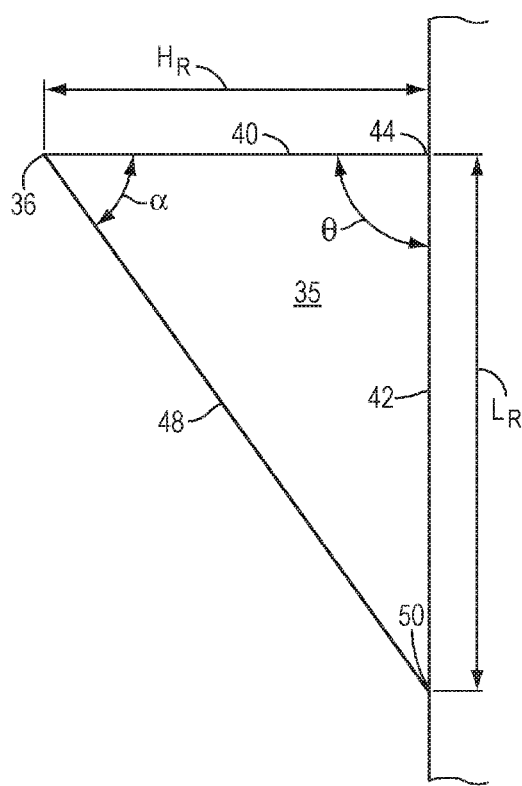
FIG. 5A is a partial longitudinal cross sectional view of an exemplary embodiment of a rib of a cannula according to the present disclosure.
Figure 5B:
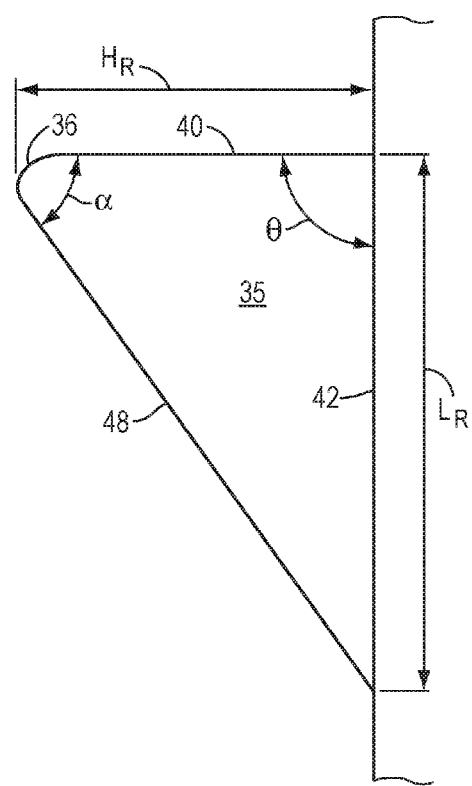
FIG. 5B is a partial longitudinal cross sectional view of another exemplary embodiment of a rib of a cannula according to the present disclosure.
Figure 5C:
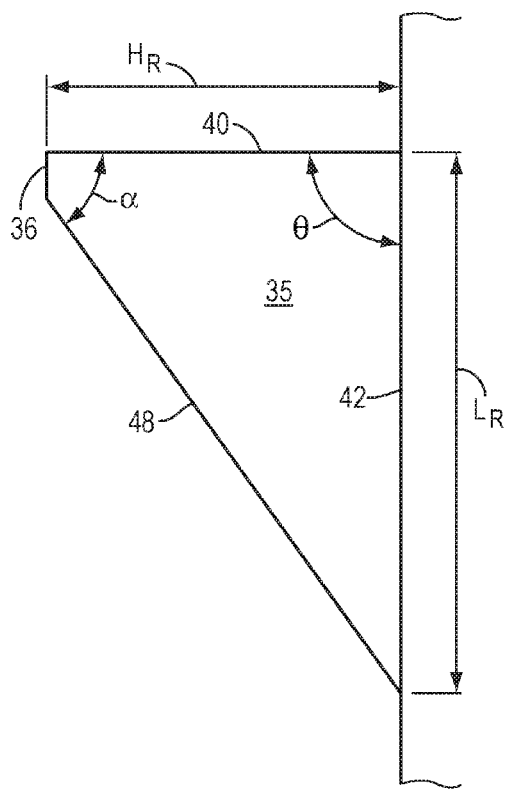
FIG. 5C is a partial longitudinal cross sectional view of another exemplary embodiment of a rib of a cannula according to the present disclosure.
Figure 5D:
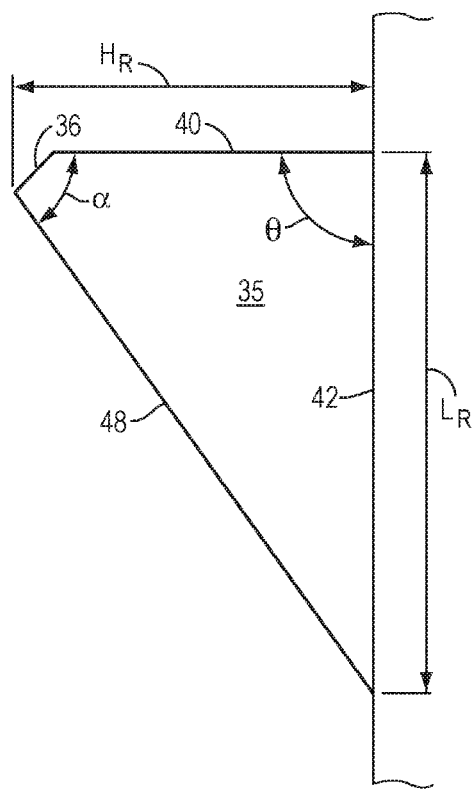
FIG. 5D is a partial longitudinal cross sectional view of yet another exemplary embodiment of a rib of a cannula according to the present disclosure.

With reference to FIG. 5A, a longitudinal cross-sectional view through one rib showing the profile of the rib relative to the outer wall of the cannula is schematically represented to illustrate various design parameters of ribs, such as ribs 235 and ribs to be described further below. Each rib 35 of FIG. 5A has a height $H_R$, a length $L_R$, and an apex 36 defining an apex angle α. As exemplified by cannula 200 (see FIG. 2B), the height $H_R$, length $L_R$, and apex angle α of each rib 35 can be the same as the height $H_R$, length $L_R$, and apex angle α of every other rib 35. Alternatively, in another exemplary embodiment in accordance with the present disclosure, the height $H_R$, length $L_R$, and/or apex angle α of each rib 35 may be varied with respect to the height $H_R$, length $L_R$, and/or apex angle α of one or more of the other ribs 35. Although the exemplary FIGS. 5A-5D show apex angle α as approximately 55 degrees, it is contemplated that the apex angle of a rib may range from about 35 degrees to about 75 degrees. The apex 36 may be pointed, as shown in FIG. 5A. Alternatively, the apex 36 may be rounded (see FIG. 5B), flattened (see FIG. 5C), or flattened and angled (see FIG. 5D).

As shown in FIG. 5A, the height $H_R$ of each rib 35 is the radial distance of each radial rib wall 40, with the rib wall 40 being the surface extending radially outward relative to the cannula longitudinal axis. The length $L_R$ of each rib 35 is the rib base 42, with the rib base 42 being the portion of the rib extending axially along the cannula from the end 44 of the radial rib wall 40. The radial rib wall 40 forms an angle θ with the rib base 42. Although FIGS. 5A-5D show angle θ as an approximate right angle, it is contemplated that the angle θ of a rib may be greater than or less than 90 degrees, for example, angle θ may range from about 70 degrees to about 110 degrees. A rib lateral wall 48 extends from the apex 36 to a second end 46 of the rib base 42. Each rib 35 may be integral with or distinct from the outer lateral wall surface (e.g., 202 of FIGS. 2A-2B) of the cannula.

Referring again to FIG. 2B, the apex of each rib 235 of the first tapered portion 208 may be incident upon an imaginary surface (shown in dotted line) that defines the first taper 206. Likewise, the apex of each rib 235 of the second tapered portion 218 may be incident upon an imaginary surface (shown in dotted line) that defines the second taper 216 and, the apex of each rib 235 of the third tapered portion 228 may be incident upon imaginary surface (shown in dotted line) that defines the third taper 226. All of the ribs 235 on cannula 200 are arranged such that, in the orientation of FIG. 2B, the lateral rib wall 48 of FIGS. 5A-5D of each rib 235 flares radially outwardly in a distal-to-proximal direction. Where, as exemplified by cannula 200, the height (i.e., $H_R$ of FIGS. 5A-5D), length (i.e., $L_R$ of FIGS. 5A-5D), and apex angle (i.e., α of FIGS. 5A-5D) of each rib 235 is the same as the height, length, and apex angle of every other rib 235, the tapers 206, 216, and 226 can be achieved by varying the thickness of the cannula wall, i.e., by varying the lateral distance between the outer lateral wall surface and the inner lateral wall surface.

In various exemplary embodiments, the present disclosure contemplates providing the cannula with indicia that assists placement of the cannula relative to the body wall of a patient in an inserted position of the cannula. By way of non-limiting example, with reference again to FIGS. 2A and 2B, a portion of the outer lateral wall surface 202 may include a central body wall target 250. The outer lateral wall surface 202 may also include an upper body wall target 252 located proximal from the central body wall target 250 and a lower body wall target 254 located distal from the central body wall target 250. The body wall targets 250, 252, 254 can provide guidance as to where the body wall should sit along the length of the cannula 200 when the cannula is inserted within the body wall of a patient. For example, it may be desirable for the body wall to be located at a region between the upper body wall target 252 and the lower body wall target 254 of the cannula 200. It may be further desirable for the body wall of a patient to be located at the central body wall target 250 of the cannula 200, in a manner similar to that depicted in FIG. 4.

By way of non-limiting example, the body wall targets 250, 252, 254 may be relied on to place cannula 200 in a desirable inserted position within the body wall of a patient by sliding the distal end of the cannula 200 through a port within the body wall, observing when the lower body wall target 254 surpasses the internal surface (i.e., distal surface) of the body wall and/or observing when the upper body wall target 252 encroaches upon the external surface (i.e., proximal surface) of the body wall, then maintaining the cannula in place relative to the body wall once one or both observations have been made.

The relative dispositions body wall targets 250, 252, 254 along the length of the cannula 200 may generally be based on the average thicknesses of the body wall of the patient or class of patients for which the cannula is intended to be used. For example, relatively short cannulas (e.g., longitudinal length of about 80 mm to about 120 mm in length) are generally deployed for surgical use on patients having a relatively narrow body wall thickness. Accordingly, the body wall targets 250, 252, 254 may be disposed on a relatively short cannula such that there is a relatively small longitudinal distance between each of the targets such that the targets provide effective guidance for cannula disposition within the body wall of a patient having a relatively narrow body wall thickness. Conversely, for example, relatively long cannulas (e.g., longitudinal length of about 20 mm to about 160 mm) are generally deployed for surgical use on patients having a relatively wide body wall thickness. Accordingly, the body wall targets 250, 252, 254 may be disposed on a relatively long cannula such that there is a relatively large longitudinal distance between each of the targets such that the targets provide effective guidance for cannula disposition within the body wall of a patient having a relatively wide body wall thickness. Alternatively, relative dispositions body wall targets 250, 252, 254 along the length of the cannula 200 may not be adjusted according to on the average thicknesses of the body wall of the patient or class of patients, such that relatively short and long cannulas may have the same or similar relative dispositions body wall targets 250, 252, 254 along the length of the cannula 200.

Thus, in making a cannula and/or waisted portion thereof in accordance with the present disclosure, the average body wall thickness of the class of patients within which it is anticipated that a cannula will be used is considered when determining the various length parameters discussed herein.

As shown in FIG. 2B, the remote center and inflection location 225 of the cannula 200 may be located at the center of the central body wall target 250. Alternatively, it is also contemplated that the center of the central body wall target of a cannula can be offset from the remote center and/or inflection location of the cannula. In exemplary embodiments having ribs, such as in FIGS. 2-4, the target indicia may be formed by regions free from ribs. However, other mechanisms for providing indicia may include colored regions or other markings on an external surface of the cannula. Those having ordinary skill in the art would appreciate numerous ways in which indicia may be provided on the cannula without departing from the scope of the present disclosure. Further, it should be understood that the exemplary embodiment of FIG. 6 may be provided with such indicia to assist in determining where to position the cannula relative to the body wall in an inserted position, even though for simplification the figure depicts no such indicia.

Figure 3A:
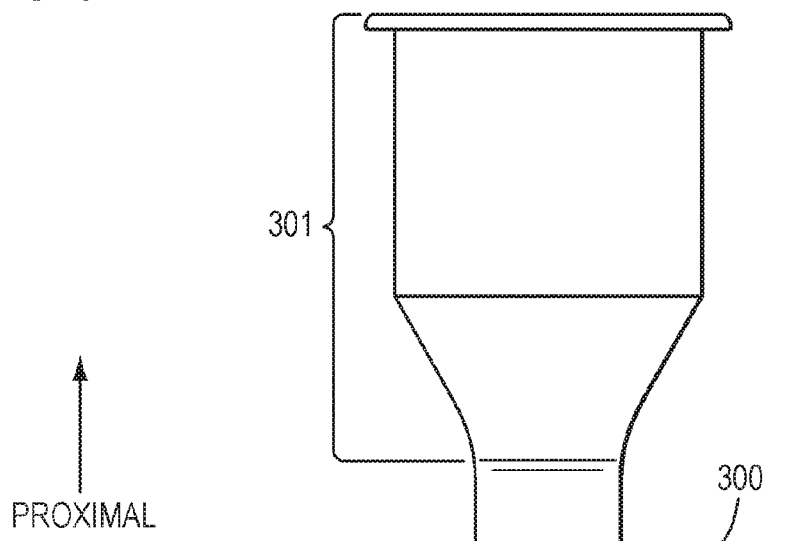
FIG. 3A is a side view of another exemplary embodiment of a cannula in accordance with the present disclosure.
Figure 3B:
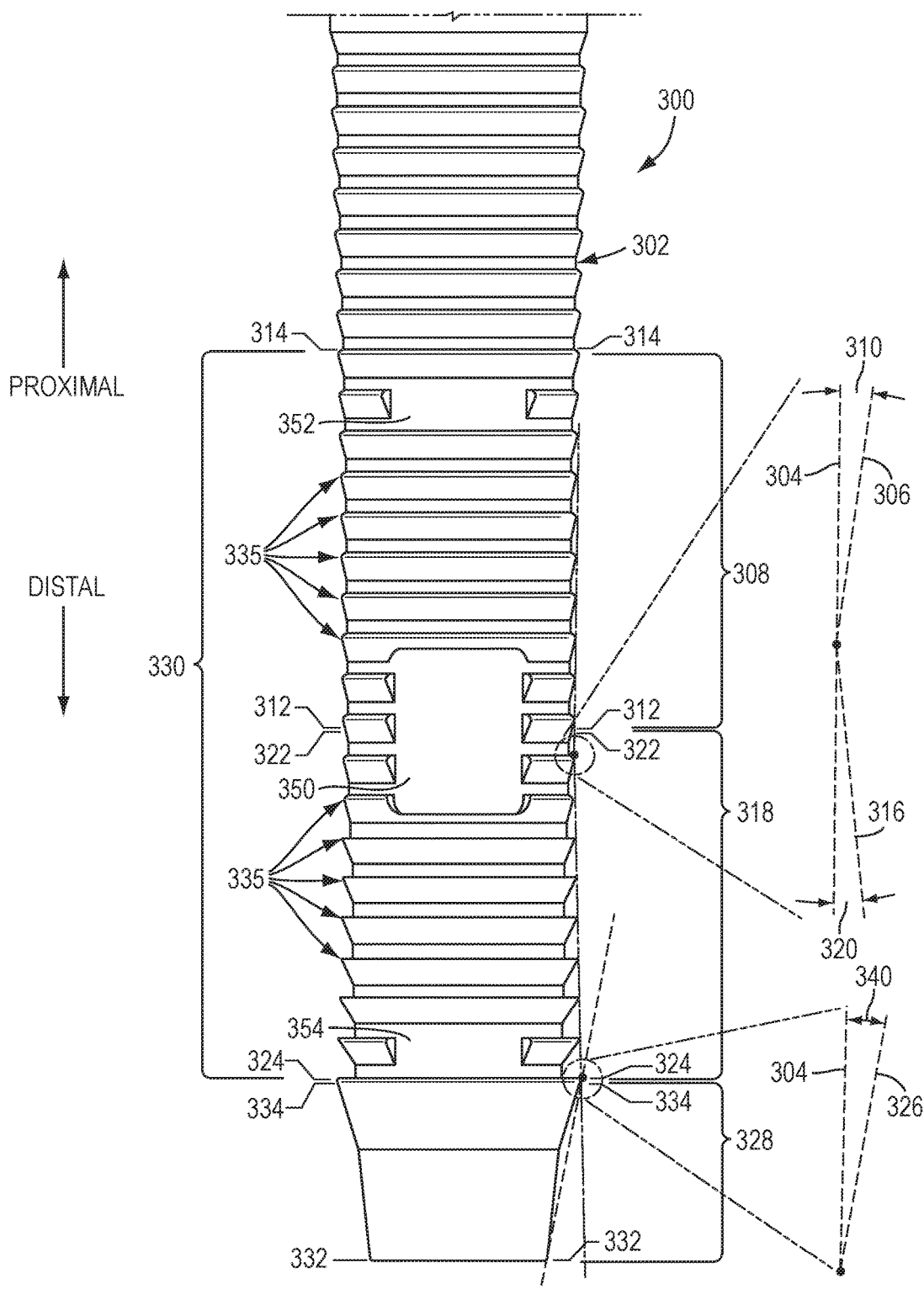
FIG. 3B is a detailed side view of the portion labeled FIG. 3B of the cannula of FIG. 3A.

With reference to FIGS. 3A-3C, an additional exemplary embodiment of cannula 300 with enhanced retention features in accordance with the present disclosure is illustrated. Cannula 300 has an inner lateral wall surface (hidden from view), that may be cylindrical or slightly tapered, in whole or in part, to enable manufacture by molding techniques, as described above. The outer lateral wall surface has a configuration that enhances retention of the cannula 300 relative to a body wall in an inserted position. Cannula 300 has outer lateral dimensions that provide a waisted portion 330. The waisted portion 330 includes a first tapered portion 308 and a second tapered portion 318. A first taper 306 defines the lateral (e.g., radial) outer limits of the first tapered portion 308 of a cannula 300. The first taper 306 has a first taper angle 310 measured relative to a longitudinal axis 304 of the cannula 300. First tapered portion 308 has a first tapered portion narrow end 312 and a first tapered portion wide end 314.

Various first taper angle 310 sizes are contemplated. For example, the size of the first taper angle 310 may be from about 1° to about 5°. The longitudinal length of the first tapered region 308 (i.e., the length of the first tapered region 308 extending from the first tapered portion narrow end 312 and a first tapered portion wide end 314) may be considered when sizing the first taper angle 310. For example, when the longitudinal length of the first tapered region 308 is relatively large (e.g., about 50 to about 100 millimeters in length), the size of the first taper angle 310 may range from about 1° to about 2°. Alternatively, for example, when the longitudinal length of the first tapered region 308 is relatively small (e.g., about 20 to about 50 millimeters in length), the size of the first taper angle 310 may range from about 2° to about 3°. In some embodiments, the size of the first taper angle 310 is about 1°.

Additionally, the outer lateral dimensions of cannula 300 include a second taper 316 that defines the lateral (e.g., radial) outer limits of the second tapered portion 318. The second taper 316 of cannula 300 has a second taper angle 320 measured relative to a longitudinal axis 304 of the cannula 300. Second tapered portion 318 has a second tapered portion narrow end 322 and a second tapered portion wide end 324.

Various second taper angle 320 sizes are contemplated. For example, the size of the second taper angle 320 may range from about −1° to about −5°. The longitudinal length of the second tapered region 318 (i.e., the length of the second tapered region extending from the second tapered portion narrow end 322 to the second tapered portion wide end 324) may be considered when sizing the second taper angle 320. For example, when the longitudinal length of the second tapered region 318 is relatively large (e.g., about 20 to 40 millimeters in length), the size of the second taper angle 320 may range from about −1° to about −2°. Alternatively, for example, when the longitudinal length of the second tapered region 318 is relatively small (e.g., about 5 to 20 millimeters in length), the size of the second taper angle 320 may range from about −2° to about −3°. In some embodiments, the size of the second taper angle 320 is about −1°.

The narrow end 312 of the first tapered portion 308 can be at approximately the same axial position as the narrow end 322 of the second tapered portion 318, although it is also contemplated that they could also be axially spaced from one another. The second tapered portion 318 and the first tapered portion 308 may be integral or distinct components. The juncture where the narrow ends 312 and 322 meet defines an inflection location 325 of the waisted portion 330. In this exemplary embodiment, the remote center of the cannula 300 is disposed at the inflection location 325.

As further depicted in FIGS. 3B and 3C, the outer lateral dimensions of cannula 300 also include a third taper 326 that defines the lateral (e.g., radial) outer limits of a third tapered portion 328 (also called third tapered region 328). Third tapered portion 328 includes a distal end of the cannula, with proximal and distal directions labeled on FIGS. 3B and 3C. The third taper 326 has a third taper angle 340 measured relative to a longitudinal axis 304 of the cannula 300. Third tapered portion 328 has a third tapered portion narrow end 332 and a third tapered portion wide end 334.

Various third taper angle 340 sizes are contemplated. For example, the size of the third taper angle 340 may range from about 1° to about 5°. The longitudinal length of the third tapered region 328 (i.e., the length of the third tapered region 328 extending from the third tapered portion narrow end 332 and a third tapered portion wide end 334) may be considered when sizing the third taper angle 340. For example, when the longitudinal length of the third tapered region 328 is relatively large (e.g., about 20 to about 50 millimeters in length), the size of the third taper angle 340 may range from about 1° to about 2°. Alternatively, for example, when the longitudinal length of the third tapered region 328 is relatively small (e.g., about 5 to about 20 millimeters in length), the size of the third taper angle 340 may range from about 2° to about 3°. In some embodiments, the size of the third taper angle 340 is about 2°.

In various embodiments, the magnitude of the size of the first taper angle 310 and the magnitude the size of the second taper angle 320 may be about the same. Further, in some embodiments, the magnitude of the size of the third taper angle 340 may be relatively larger than the magnitude of the size of the first taper angle 210 and/or the magnitude the size of the second taper angle 320. Thus, in various exemplary embodiments, the size of the first taper angle 310 ranges from about 1° to about 2°, the size of the second taper angle 320 range from about −1° to about −2°, and the size of the third taper angle 340 ranges from about 2° to about 3°.

Accordingly, in an exemplary embodiment, the size of the first taper angle 310 is about 1°, the size of the second taper angle 320 ranges about −1°, and the size of the third taper angle 340 is about 2°.

The wide end 324 of the second tapered portion 318 may be collocated or slightly axially spaced from the wide end 334 of the third tapered portion 328. The second tapered portion 318 and the third tapered portion 328 may be integral or distinct components.

In an alternative embodiment, it is envisioned as within the scope of the present disclosure that instead of having the third taper 326, the cannula 300 can have outer lateral dimensions such that the cannula outer surface extends straight from wide end 324 of the second tapered portion 318 to the distal end of the cannula 300.

As shown in FIG. 3B, the waisted portion 330 thus may extend from a waist proximal end at first tapered portion wide end 314 to a waist distal end at the second tapered portion wide end 324. Further, the end 332 is the distal end of the cannula 300. A cannula according to the present disclosure further can include additional portions that extend proximally from wide end 314 and/or distally from the wide end 324 such that the proximal end of the cannula 300 is beyond wide end 314 and/or the distal end of the cannula 300 is beyond the wide end 324.

Cannula 300 also includes radially protruding ribs 335 extending from the outer lateral wall surface 302. In FIGS. 3A-3C, adjacent ribs 335 are uniformly spaced apart in the axial direction. Alternatively, the ribs 335 of a cannula in accordance with the present disclosure can be non-uniformly spaced, i.e. the space between each adjacent ribs can vary with respect to the space between one or more other adjacent ribs. The total number of ribs 335 on the cannula 300 also can vary. Also, the number of ribs 335 within each portion 308, 318, and 328 may be varied. Moreover, as shown in the figures, in various exemplary embodiments that include ribs, it is contemplated that a distal end portion be free of ribs so as to facilitate a smooth insertion of the cannula into an incision or other opening in the body wall. Further, as shown in FIG. 3A, in an exemplary embodiment, the cannula 300 can be free of ribs along a portion of the cannula tube extending from the cannula bowl 301 to a location proximal or starting at the proximal end of the waisted portion 330.

Similar to the exemplary embodiment of FIGS. 2A-2C, a portion of the outer lateral wall surface 302 of cannula 300 includes a body wall targets, such as central body wall target 350, upper body wall target 352 located proximal to the central body wall target 350, and lower body wall target 354 located distal to the central body wall target 350. As shown in FIG. 3B, the body wall targets 350, 352, 354 may be defined by a gap in some of the ribs 335 of the cannula 300. The body wall targets 350, 352, 354 can provide guidance as to an intended positioning of the cannula with respect to the body wall along the length of the cannula 300 in the inserted position of the cannula. For example, it may be desirable for the body wall to be located at a region between the upper body wall target 352 and the lower body wall target 354 of the cannula 300. It may be further desirable for the body wall of a patient to be located approximately at the central body wall target 350 of the cannula 300. As shown in FIG. 3B, the remote center and inflection location 325 of the cannula 300 may be at the center of the central body wall target 350. Alternatively, it is also contemplated that the center of the central body wall target of a cannula can be offset from the remote center and/or inflection location of the cannula.

Referring again to FIG. 3C, the apex of each rib 335 of the first tapered portion 308 is incident upon an imaginary surface (shown in dotted line) that defines the first taper 306 of cannula 300. Likewise the apex of each rib 335 of the second tapered portion 318 is incident upon an imaginary surface (shown in dotted line) that defines the second taper 316 of cannula 300, and the apex of each rib 335 of the third tapered portion 328 may be incident upon an imaginary surface (shown in dotted line) that defines the third taper 326. Along a longitudinal cross-sectional plane of the cannula 300, the outer lateral wall surface 302 may be substantially parallel to first taper 306 along the entire longitudinal length of the cannula, and therefore non-parallel to second and third tapers 316 and 326. In other words, the orientation of outer lateral wall surface 302 along a longitudinal cross-sectional plane of the cannula 300 may be parallel with first taper 306 throughout the length of the cannula 300 such that it is not parallel to orientation of the tapers 316 and 326 within any of the tapered portions 308, 318, and 328. In various embodiments, the size of the first taper angle 310 may range from about 1° to about 5°, as set forth above. In other various embodiments, the size of the first taper angle 310 may be about 0° such that the orientation of the first taper 306, as well as the orientation of outer lateral wall surface 302, are parallel to the longitudinal axis 304 throughout the length of the first portion 308 along a longitudinal cross-sectional plane of the cannula 300. Moreover, in some exemplary embodiments, along a longitudinal cross-sectional plane of the cannula 300, the outer lateral wall surface 302 may be slightly tapered at an angle that is not the same as the size of the first taper angle 310, such that the outer lateral wall surface is tapered along the entire longitudinal length of the cannula and yet nonparallel to first taper 306, as well as non-parallel to second and third tapers 316 and/or 326.

In the embodiment of FIGS. 3A-3C, in order for all apexes of ribs 335 to be incident upon differently oriented tapers 306 and 316, and thereby provide a waisted configuration of the cannula 300, the height (i.e., $H_R$ in FIGS. 5A-5D) and apex angle α (i.e., α in FIGS. 5A-5D) of each rib 335 is varied along the length of the waisted portion 330 of the cannula 300. As illustrated in FIG. 3C, each rib 335 of the first tapered portion 308 may have a different apex angle $\alpha_{308a}$-$\alpha_{308e}$, respectively, and each rib 335 of the first tapered portion 318 may have a different apex angle $\alpha_{318a}$-$\alpha_{318h}$, respectively. The value of the first tapered portion apex angles $\alpha_{308a}$-$\alpha_{308e}$ may gradually decrease from $\alpha_{308a}$ to $\alpha_{308e}$ such that the apex of each rib 335 of the first tapered portion 308 is incident upon the imaginary surface defining the first taper 306, even though the outer lateral wall surface 302 is nonparallel to taper 306. Likewise, the value of the second tapered portion apex angles $\alpha_{318a}$-$\alpha_{318e}$ may gradually decrease from $\alpha_{308a}$ to $\alpha_{308e}$ such that the apex 336 of each rib 335 of the second tapered portion 318 is incident upon the imaginary surface defining second taper 316, even though the outer lateral wall surface 302 is nonparallel to the taper 316.

Figure 7:
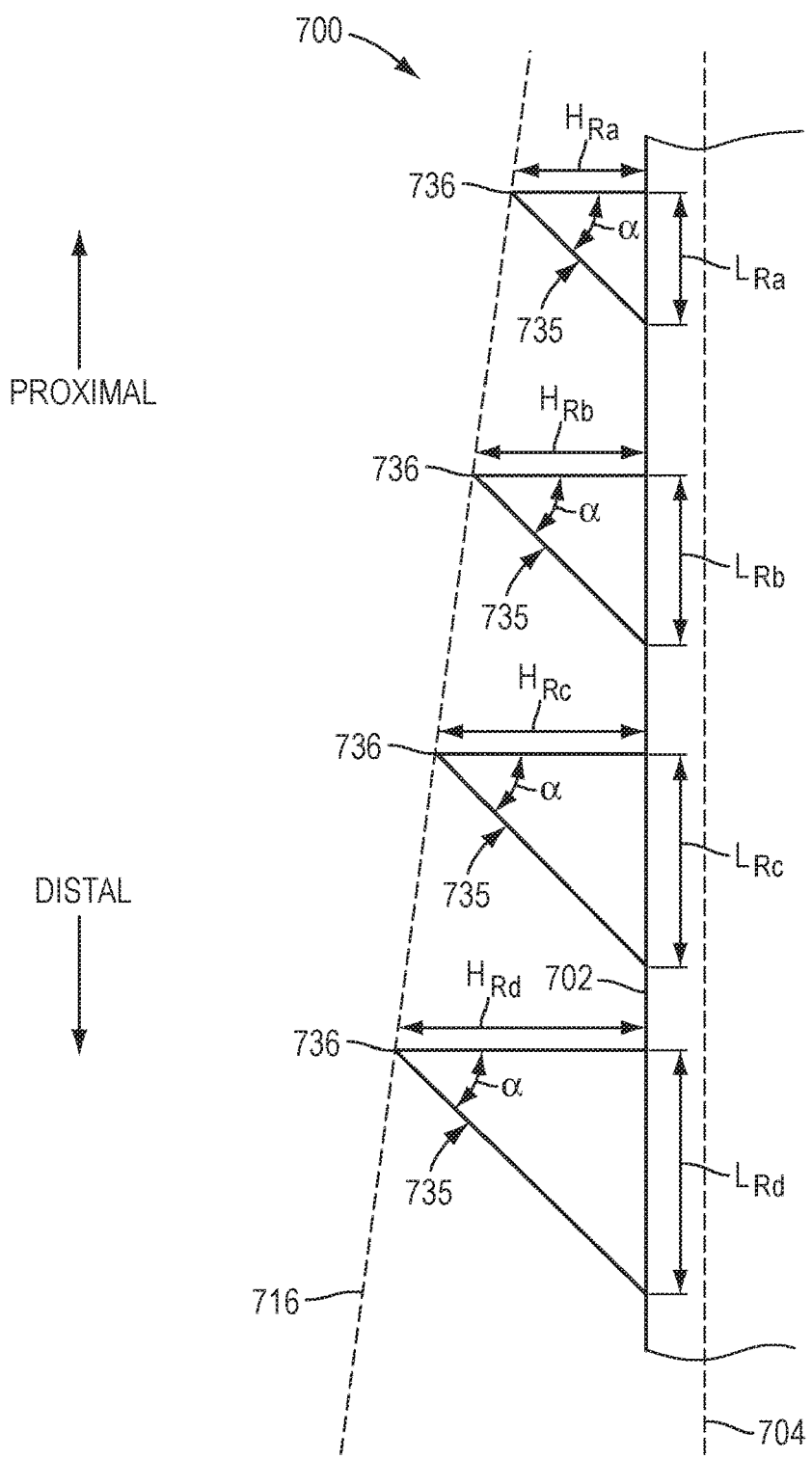
FIG. 7 is a partial longitudinal cross sectional view of an exemplary embodiment of a configuration of ribs of a cannula according to the present disclosure.

As illustrated in FIGS. 3A-3C, the length (i.e., $L_R$ in FIGS. 5A-5D) of each rib 335 may be equal to the length of every other rib 335. However, in an alternative embodiment in accordance with the present disclosure, where the outer lateral wall surface (i.e., 302 in FIGS. 3B-3C) is nonparallel to the orientation of one or more of the tapers (i.e., 306, 316, and 326 in FIGS. 3B-3C), the length (i.e., $L_R$ in FIGS. 5A-5D) and height (i.e., $H_R$ in FIGS. 5A-5D) of each rib may be varied along the length of the cannula such that the apexes (i.e., 36 in FIGS. 5A-5D) of the ribs are incident upon the respective imaginary surfaces defining the one or more tapers, and the apex angle (i.e., α in FIGS. 5A-5D) of each rib may be equal to the apex angle of every other rib. For example, turning to FIG. 7, a longitudinal cross-sectional view through a series of ribs 735 showing the profile of the ribs 735 relative to the outer wall 702 of the cannula 700 is schematically represented to illustrate an alternative configuration of ribs along a cannula within the scope of the present disclosure. The outer lateral wall surface 702 is nonparallel to orientation the taper 716 because the lengths $L_{Ra}$-$L_{Rd}$ in FIGS. 5A-5D) and heights $H_{Ra}$-$H_{Rd}$ of each rib 735 vary along the length of the cannula such that the apex 736 of each rib 735 is incident upon the respective imaginary surfaces defining the taper 716, and the apex angle α of each rib 735 is the same. The outer lateral wall surface 702 may be parallel to the longitudinal axis 704 or the outer lateral wall surface 702 may be slightly tapered relative to the longitudinal axis 704, as described above. With respect to cannula 700, the length of the ribs 735 gradually increases from $L_{Ra}$ to $L_{Rd}$ in a distal direction and the height of the ribs 735 gradually increases from $H_{Ra}$ to $H_{Rd}$ in a distal direction. To provide a taper in the direction from proximal to distal (not shown in FIG. 7), the length and height of the ribs may decrease in the distal direction, while each rib has the same apex angle.

Figure 8:
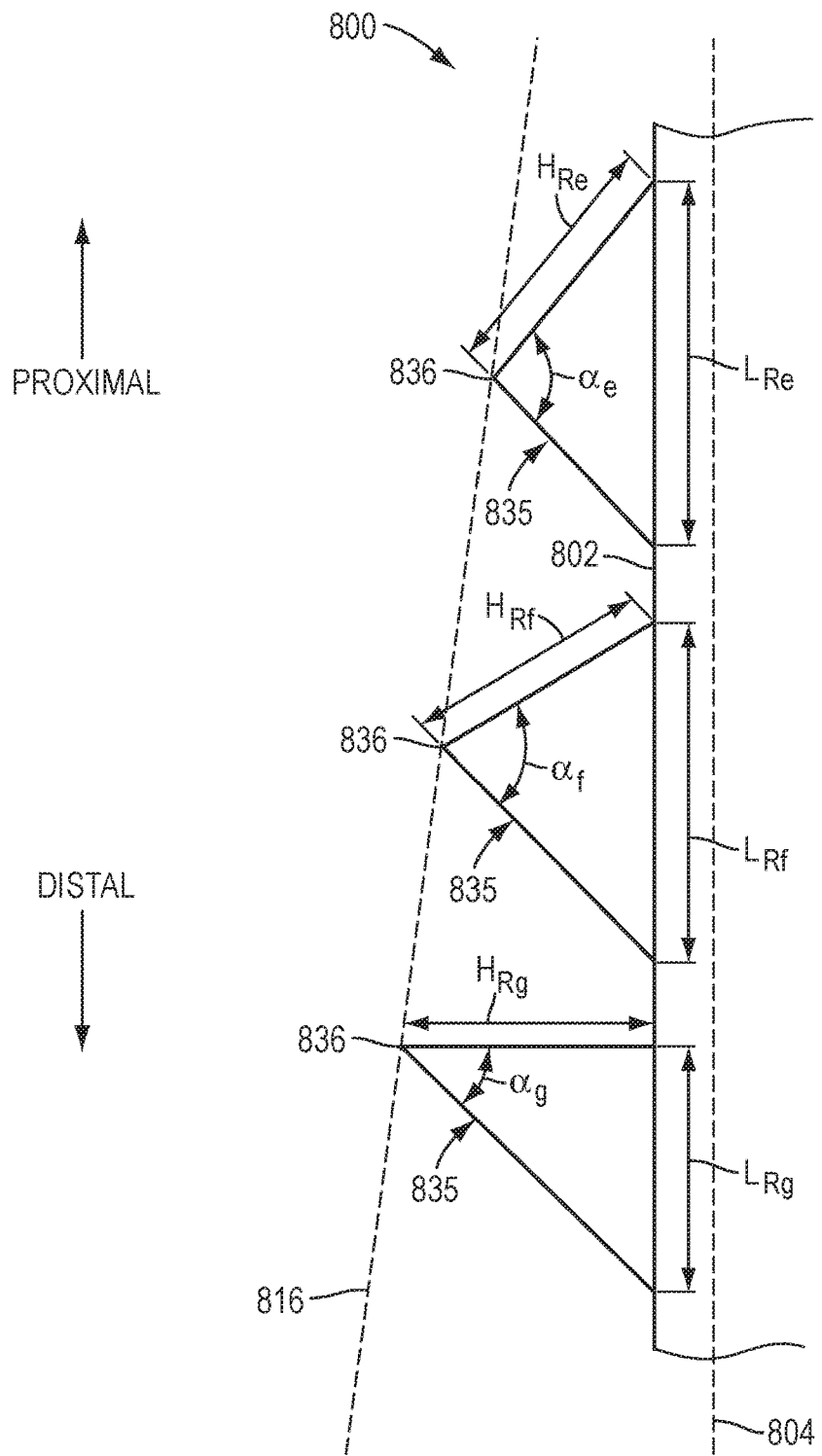
FIG. 8 is a partial longitudinal cross sectional view of another exemplary embodiment of a configuration of ribs of a cannula according to the present disclosure.

In another alternative embodiment in accordance with the present disclosure, where the outer lateral wall surface (i.e., 302 in FIGS. 3B-3C) is nonparallel to orientation of one or more tapers (i.e., 306, 316, and 326 in FIGS. 3B-3C), the length (i.e., $L_R$ in FIGS. 5A-5D) and apex angle (i.e., α in FIGS. 5A-5D) of each rib may vary along the length of the cannula such that the apexes (i.e., 36 in FIGS. 5A-5D) of the ribs are incident upon the respective imaginary surfaces defining the one or more tapers, and the height (i.e., $H_R$ in FIGS. 5A-5D) of each rib may be equal to the height of every other rib. For example, turning to FIG. 8, a longitudinal cross-sectional view through a series of ribs 835 showing the profile of the ribs 835 relative to the outer wall 802 of the cannula 800 is schematically represented to illustrate an alternative configuration of ribs along a cannula within the scope of the present disclosure. The outer lateral wall surface 802 is nonparallel to orientation the taper 816 because the lengths $L_{Re}$-$L_{Rg}$ and apex angles $\alpha_g$-$\alpha_g$ of each rib 835 are varied along the length of the cannula such that the apex 836 of each rib 835 is incident upon the respective imaginary surfaces defining the taper 816, and the height $H_R$ of each rib 835 is the same. The outer lateral wall surface 802 may be parallel to the longitudinal axis 804 or the outer lateral wall surface 802 may be slightly tapered relative to the longitudinal axis 804, as described above. With respect to cannula 800, the lengths of the ribs 35 gradually increase from $L_{Re}$ to $L_{Rg}$ in a distal direction and the apex angles of the ribs 835 gradually decrease from $\alpha_g$ to $\alpha_g$ in a distal direction, while each rib has the same height $H_R$. To provide a taper in the proximal to distal direction (not shown in FIG. 8), the apex and length of the ribs may increase in distal direction, while each rib has the same height.

Figure 9:
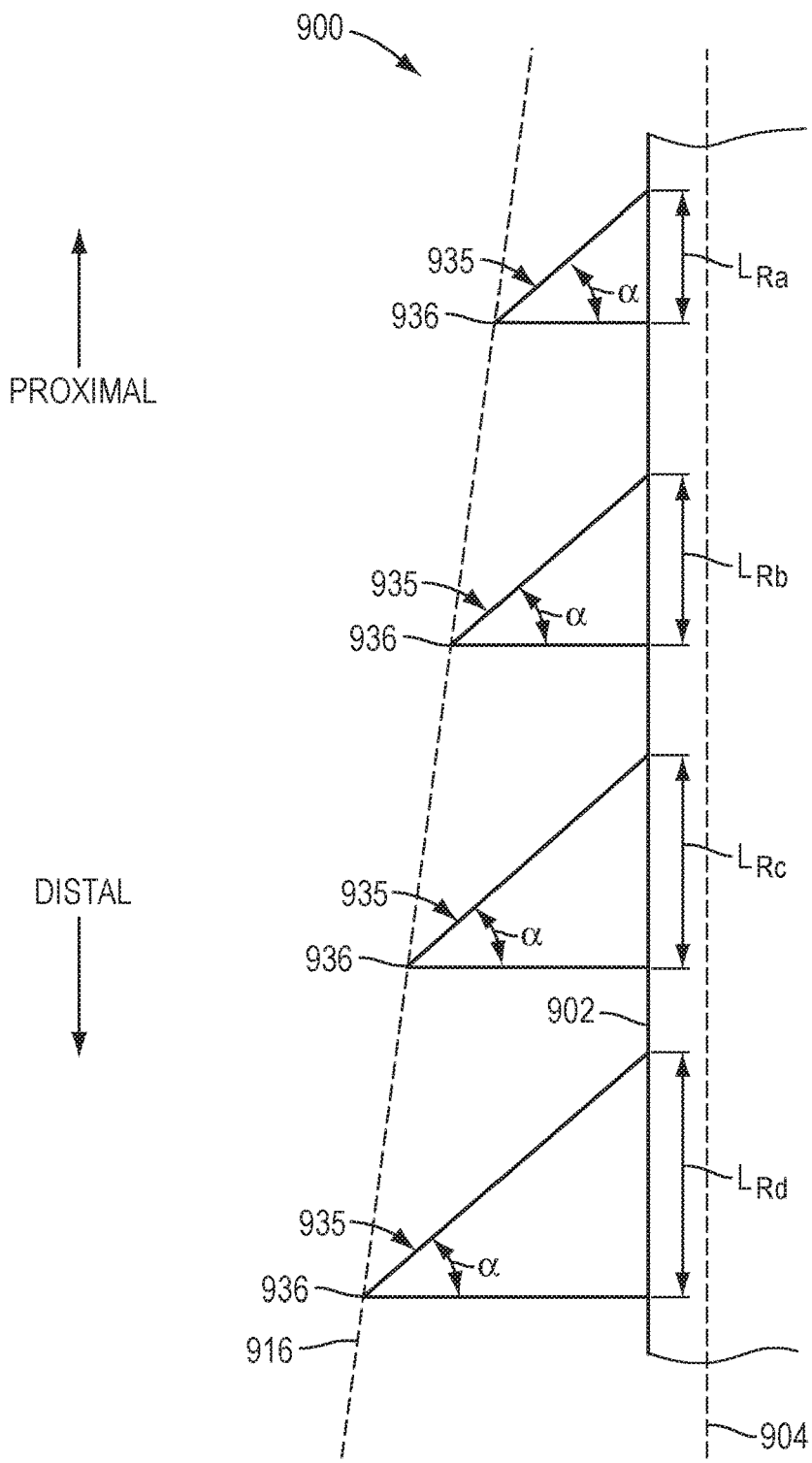
FIG. 9 is a partial longitudinal cross sectional view of another exemplary embodiment of a configuration of ribs of a cannula according to the present disclosure.
Figure 10:
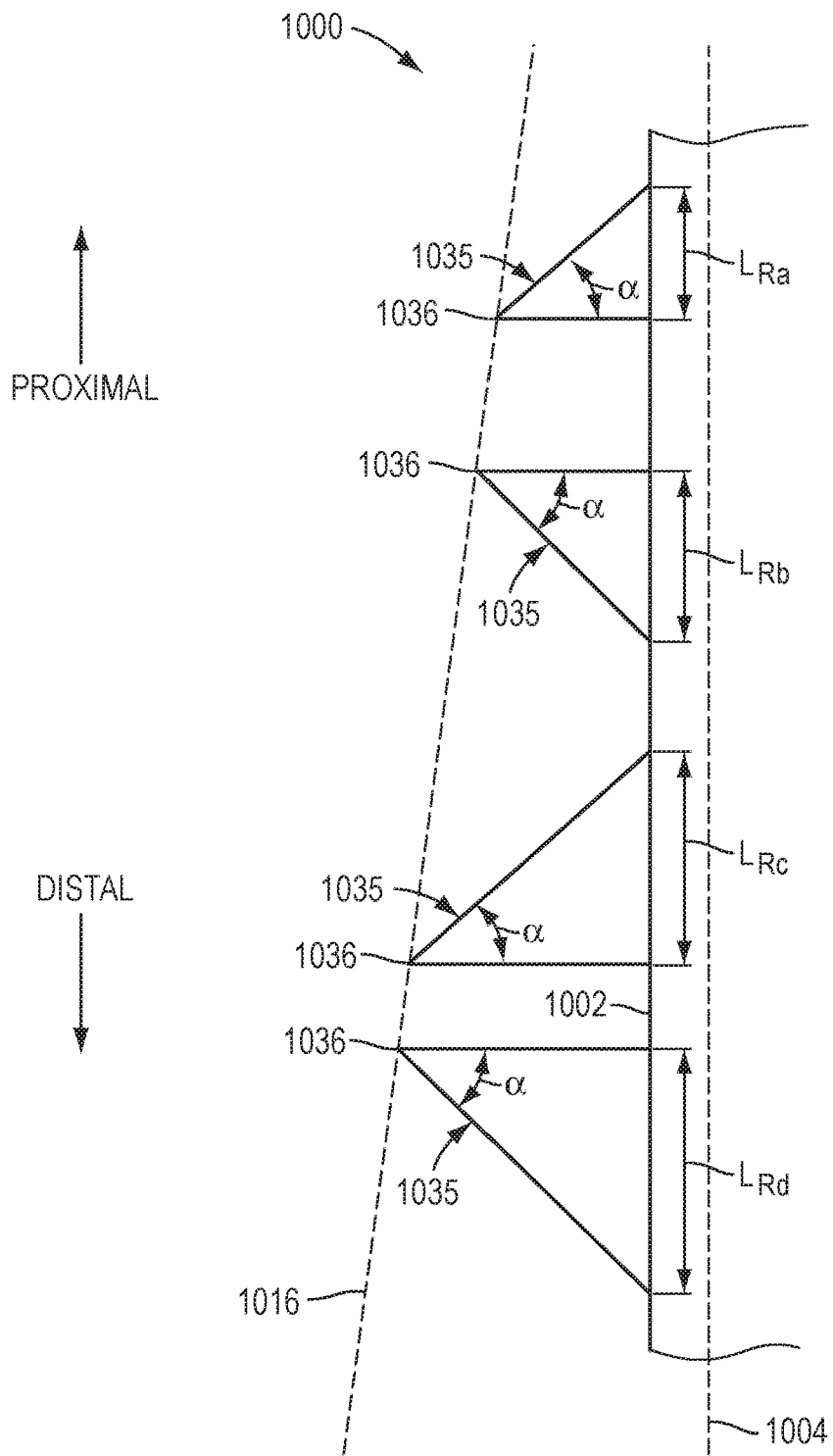
FIG. 10 is a partial longitudinal cross sectional view of yet another exemplary embodiment of a configuration of ribs of a cannula according to the present disclosure.

According to yet another exemplary embodiment, to provide further increased retention force, ribs along different portions of the length of the cannula may be oriented in a "reverse" manner from each other. For example, ribs 235, 335 of the first tapered portion 208, 308, the ribs 235, 335 of the second taper portion 218, 318 and/or the ribs 235, 335 of the third tapered portion 228, 338 may be "reversed" such that when the distal end of the cannula 200, 300 is oriented below the proximal end of the cannula, the radial rib wall (i.e., 40 of FIGS. 5A-5D) of each rib 235, 335 is disposed below the rib base (i.e., 42 of FIGS. 5A-5D) and the rib lateral wall 48 (i.e., 48 of FIGS. 5A-5D). Reference is made to FIG. 9 schematically illustrating an exemplary embodiment of a cannula having each rib 935 oriented in a reverse manner, and to FIG. 10 schematically illustrating another exemplary embodiment of a cannula having ribs 1035 that are alternately oriented in different directions. In other words, ribs in one or more tapered portions (e.g., tapered portions 208, 218, and 228 of cannula 200) of a cannula may be arranged such that, in the orientation of FIGS. 2A-3C, the radial rib wall (i.e., 48 of FIGS. 5A-5D) of each rib tapers radially inwardly in a distal-to-proximal direction. Similarly, those having ordinary skill in the art also would appreciate that some or all of the ribs of a cannula (e.g., ribs 235, 335) may have a "reverse" orientation from what is shown in FIGS. 2-5.

In some exemplary embodiments, ribs 235, 335 in the first tapered portion 208, 308 of cannula 200, 300 are arranged such that, in the orientation of FIGS. 2A-3C, the radial rib wall (i.e., 48 of FIGS. 5A-5D) of each rib 235, 335 tapers radially inwardly in a distal-to-proximal direction ("reverse" orientation), and ribs 235, 335 in the second tapered portion 218, 318 and the second tapered portion 228, 328 of cannula 200, 300 are arranged such that, in the orientation of FIGS. 2A-3C, the radial rib wall (i.e., 48 of FIGS. 5A-5D) of each rib 235, 335 tapers radially inwardly in a proximal-to-distal direction ("non-reverse" orientation that is the same as what is shown in FIGS. 2-5). Utilizing such "reversed" ribs within the first tapered portion deters insertion of the cannula 200, 300 beyond the inflection location 225, 325. Accordingly, such an arrangement encourages proper disposition of the cannula relative to the body wall during insertion and facilitates retention of the cannula in an inserted position within the body wall during a surgical procedure.

The rib configurations shown in FIGS. 5A-5D, 7, 8, 9, and 10 are to be taken as non-limiting examples of the possible rib configurations and geometry for a ribbed cannula in accordance with the present disclosure. For example, although FIGS. 5A-5D, 7, 8, 9, and 10 are discussed as displaying exemplary longitudinal cross sectional geometry of longitudinally spaced, annular ribs (i.e., ring-shaped ribs), ribs of a cannula according to the present disclosure may alternatively take the form of helical threads.

Figure 12:
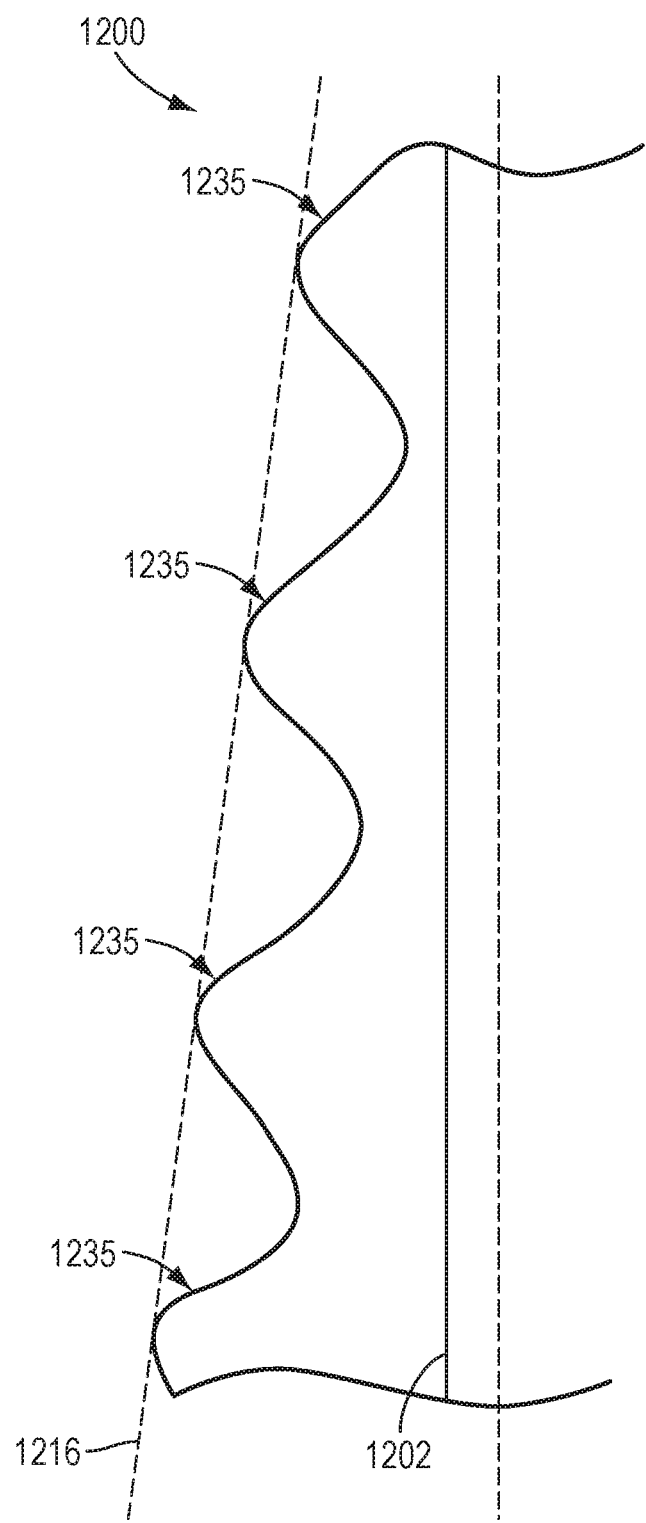
FIG. 12 is a partial longitudinal cross sectional view of an exemplary embodiment of a configuration of ribs of a cannula according to the present disclosure.

Moreover, in addition to those shown in FIGS. 5A-5D, 7, 8, 9, and 10, alternative longitudinal cross sectional geometry of the ribs of a cannula according to the present disclosure is also contemplated. For example, with reference to FIG. 12, a longitudinal cross-sectional view through a series of ribs 1235 showing the profile of the ribs 1235 relative to the outer wall 1202 of the cannula 1200 is schematically represented to illustrate an alternative configuration of ribs along a cannula within the scope of the present disclosure. Ribs 1235 of a cannula according to the present disclosure are configured to have a sine-like waveform cross section with each rib 1235 being incident upon the respective imaginary surfaces defining the taper 1216.

Figure 13:
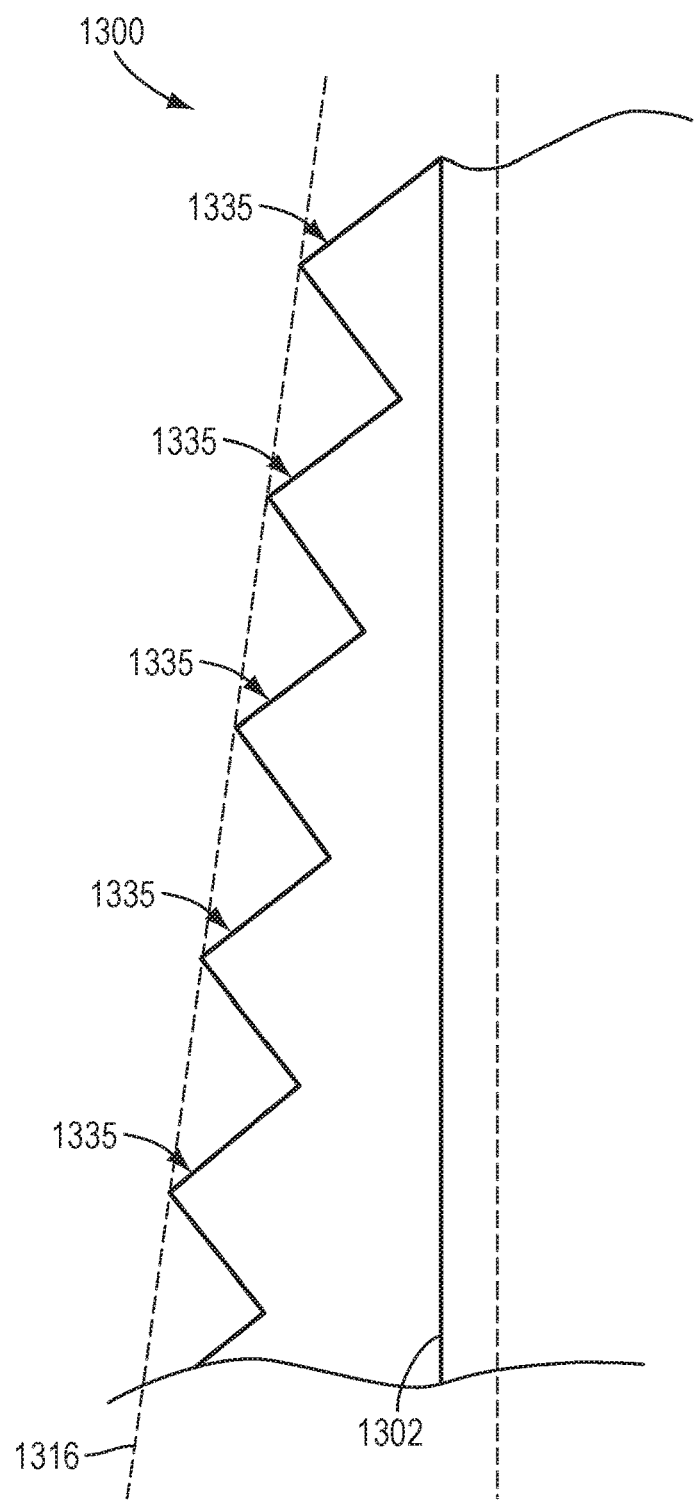
FIG. 13 is a partial longitudinal cross sectional view of another exemplary embodiment of a configuration of ribs of a cannula according to the present disclosure.

Turning to FIG. 13, a longitudinal cross-sectional view through a series of ribs 1335 showing the profile of the ribs 1335 relative to the outer wall 1302 of the cannula 1300 is schematically represented to illustrate another alternative configuration of ribs along a cannula within the scope of the present disclosure. Ribs 1335 of cannula 1300 are configured to have a triangle waveform cross section with each rib 1335 being incident upon the respective imaginary surfaces defining the taper 1316.

Figure 14:
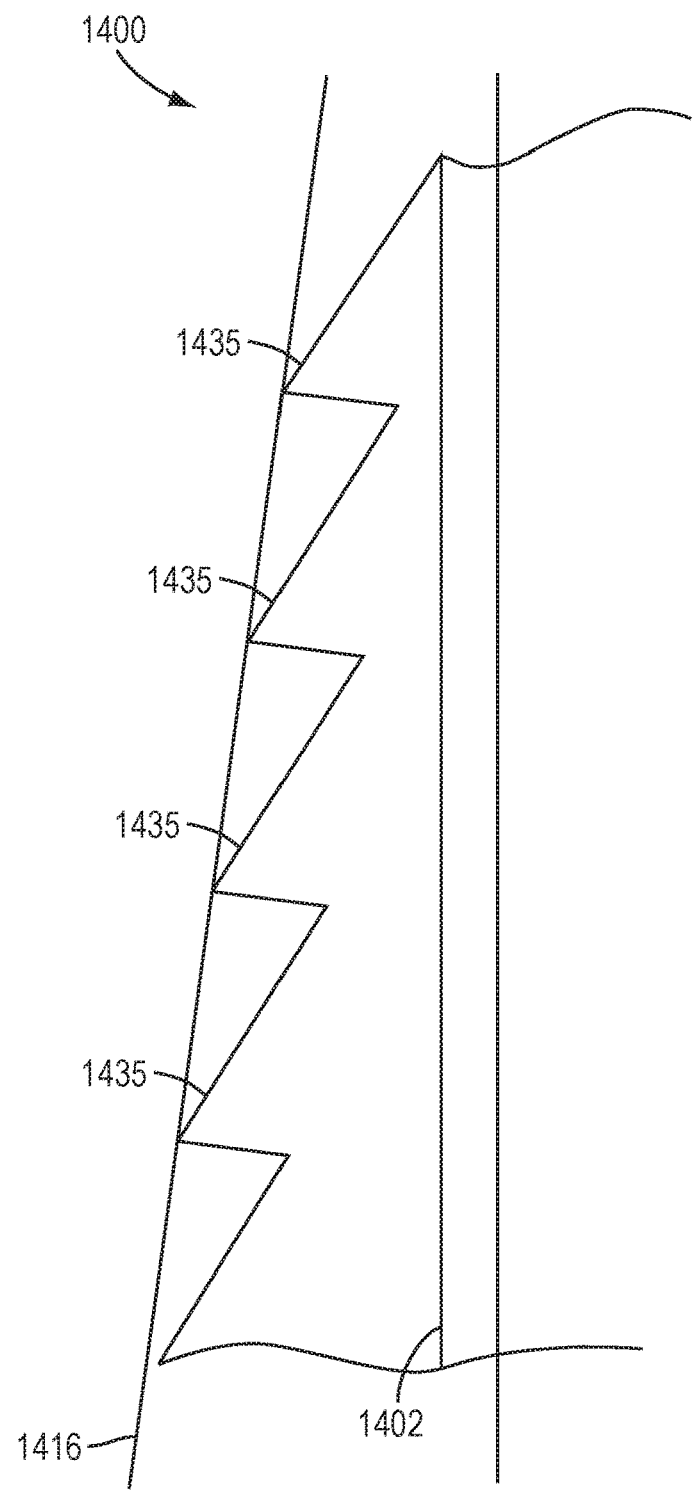
FIG. 14 is a partial longitudinal cross sectional view of another exemplary embodiment of a configuration of ribs of a cannula according to the present disclosure.

With reference to FIG. 14, a longitudinal cross-sectional view through a series of ribs 1435 showing the profile of the ribs 1435 relative to the outer wall 1402 of the cannula 1400 is schematically represented to illustrate another alternative configuration of ribs along a cannula within the scope of the present disclosure. Ribs 1435 of cannula 1400 are configured to have a saw-tooth waveform cross section with each rib 1435 being incident upon the respective imaginary surfaces defining the taper 1416.

Figure 15:
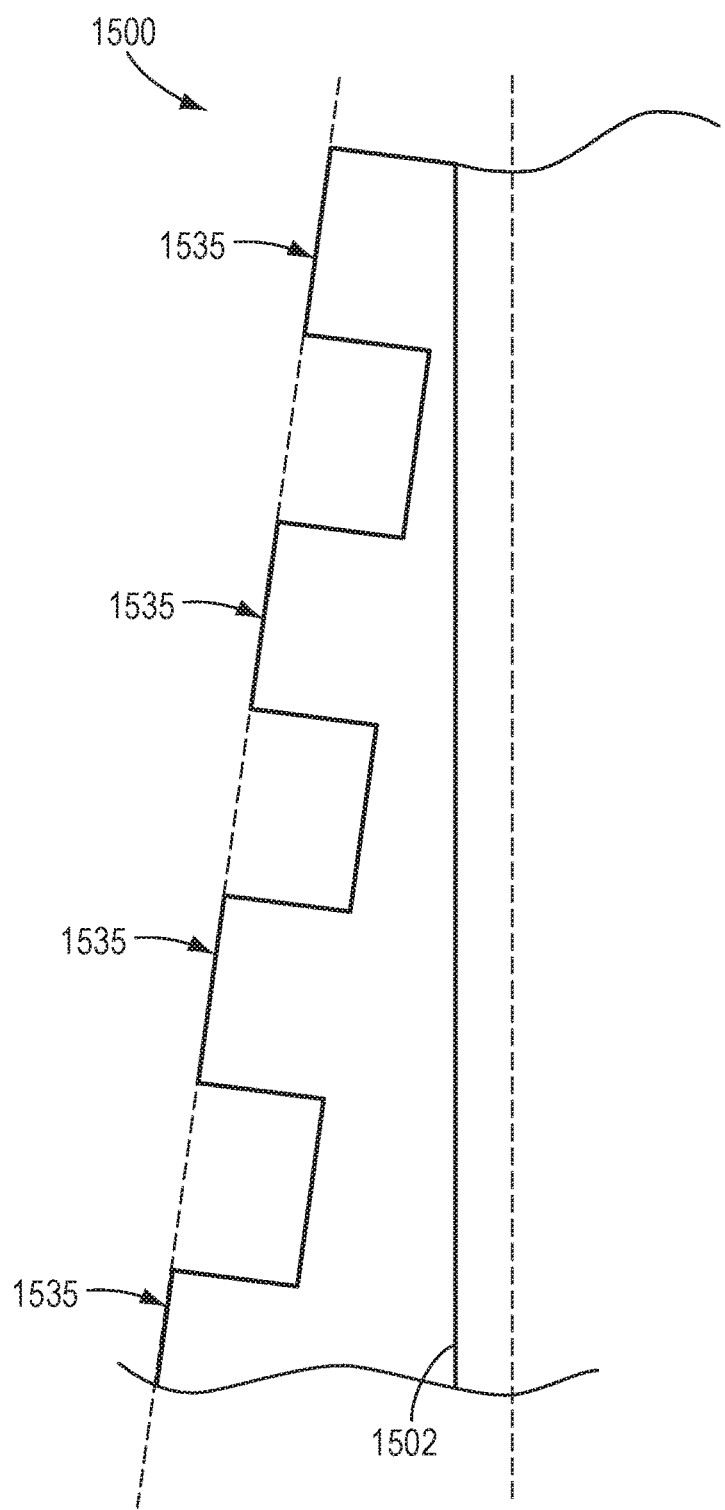
FIG. 15 is a partial longitudinal cross sectional view of yet another exemplary embodiment of a configuration of ribs of a cannula according to the present disclosure.

Turning to FIG. 15, a longitudinal cross-sectional view through a series of ribs 1535 showing the profile of the ribs 1535 relative to the outer wall 1502 of the cannula 1500 is schematically represented to illustrate another alternative configuration of ribs along a cannula within the scope of the present disclosure. Ribs 1535 of cannula 1500 are configured to have a rectangle waveform cross section with each rib 1535 being incident upon the respective imaginary surfaces defining the taper 1516.

Figure 6A:
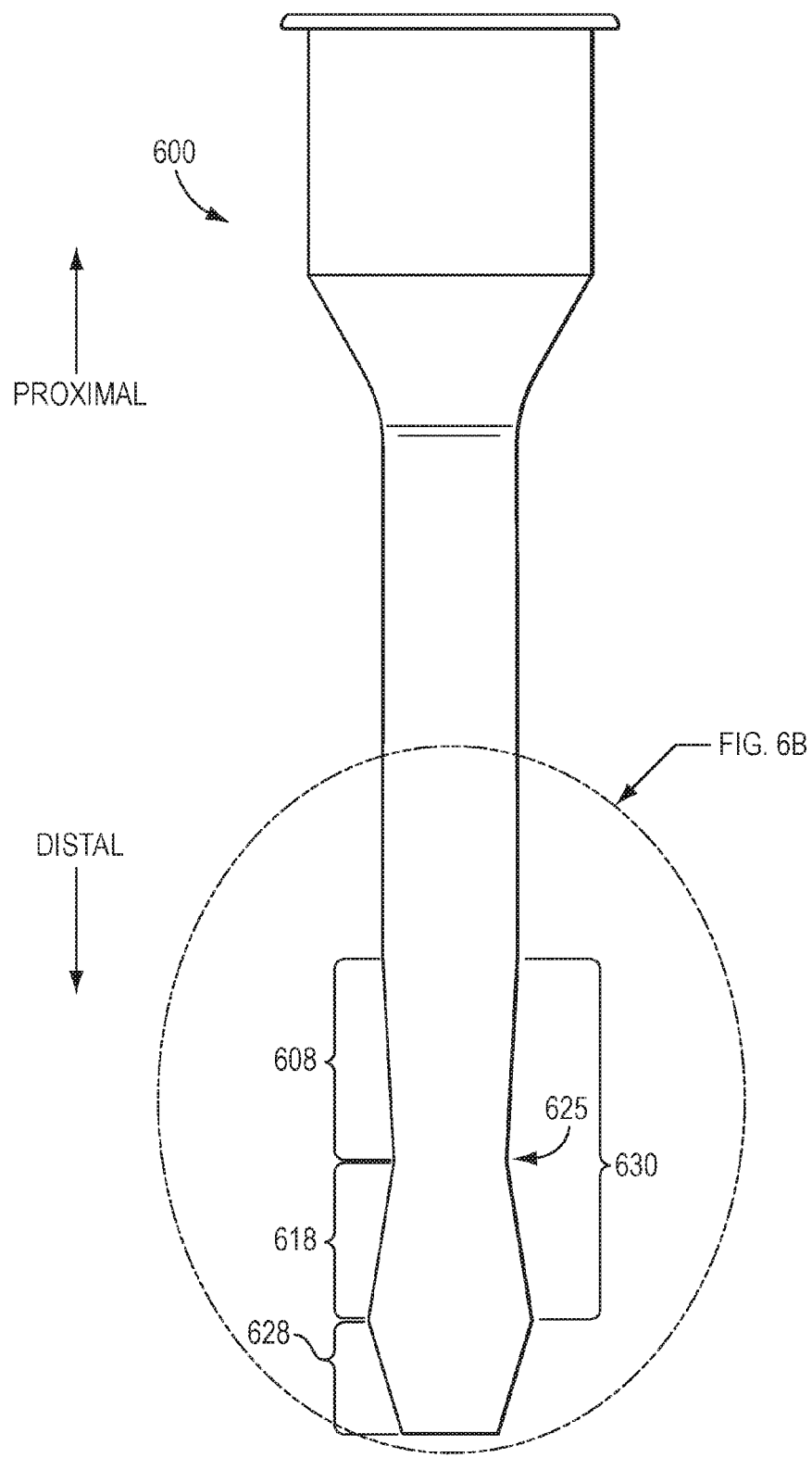
FIG. 6A is a side view of yet another exemplary embodiment of a cannula in accordance with the present disclosure.
Figure 6B:
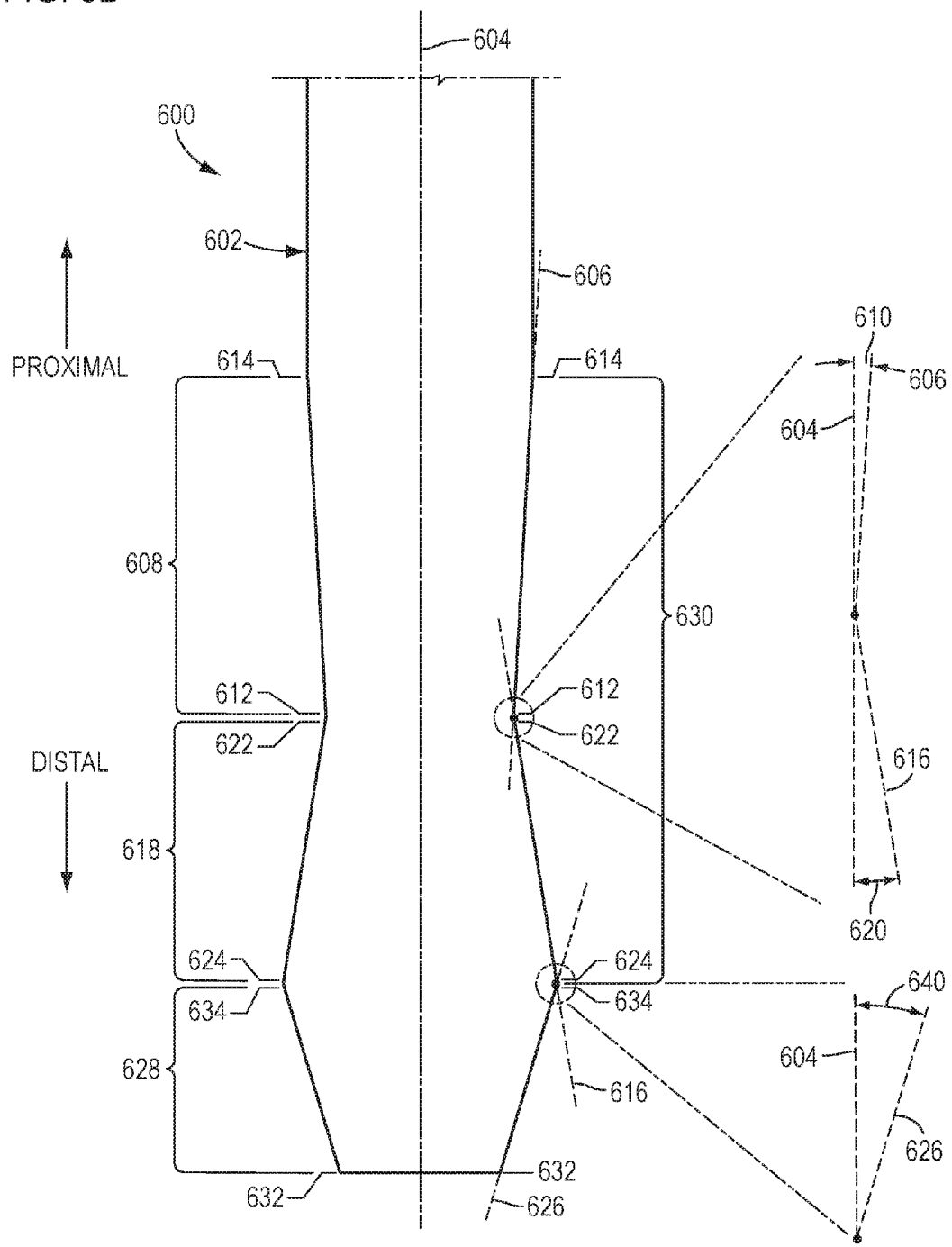
FIG. 6B is a detailed side view of the portion labeled FIG. 6B of the cannula of FIG. 6A.

With reference to FIGS. 6A-6B, an additional exemplary embodiment of cannula 600 with enhanced retention feature in accordance with the present disclosure is illustrated. Cannula 600 has a lateral inner wall surface (hidden from view), that may be shaped the same as described above. The outer lateral wall surface has a configuration that enhances retention of the cannula 600 relative to a body wall in an inserted position. Similar to the exemplary embodiments of FIGS. 2 and 3, cannula 600 has outer lateral dimensions that define a waisted portion 630. The waisted portion 630 includes a first tapered portion 608 (also called first tapered region 608) and a second tapered portion 618 (also called second tapered region 618). A first taper 606 defines the lateral (e.g., radial) outer limits of the first tapered portion 608. The first taper 606 has a first taper angle 610 measured relative to a longitudinal axis 604 of the cannula 600. First tapered portion 608 has a first tapered portion narrow end 612 and a first tapered portion wide end 614.

Various first taper angle 610 sizes are contemplated. For example, the size of the first taper angle 610 may range from about 1° to about 5°. The longitudinal length of the first tapered region 608 (i.e., the length of the first tapered region 608 extending from the first tapered portion narrow end 612 and a first tapered portion wide end 614) may be considered when sizing the first taper angle 610. For example, when the longitudinal length of the first tapered region 608 is relatively large (e.g., about 50 to about 100 millimeters in length), the size of the first taper angle 610 may range from about 1° to about 2°. Alternatively, for example, when the longitudinal length of the first tapered region 608 is relatively small (e.g., about 20 to about 50 millimeters in length), the size of the first taper angle 610 may range from about 2° to about 3°. In some embodiments, the size of the first taper angle 610 is about 1°.

Additionally, a second taper 616 defines the lateral (e.g., radial) outer limits of the second tapered portion 618 of the cannula 600. The second taper 616 of the cannula 600 has a second taper angle 620 measured relative to the longitudinal axis 604 of the cannula 600. Second tapered portion 618 has a second tapered portion narrow end 622 and a second tapered portion wide end 624.

Various second taper angle 620 sizes are contemplated. For example, the size of the second taper angle 620 may range from about −1° to about −5°. The longitudinal length of the second tapered region 618 (i.e., the length of the second tapered region extending from the second tapered portion narrow end 622 to the second tapered portion wide end 624) may be considered when sizing the second taper angle 620. For example, when the longitudinal length of the second tapered region 618 is relatively large (e.g., about 20 to 40 millimeters in length), the size of the second taper angle 620 may range from about −1° to about −2°. Alternatively, for example, when the longitudinal length of the second tapered region 618 is relatively small (e.g., about 5 to about 20 millimeters in length), the size of the second taper angle 620 may range from about −2° to about −3°. In some embodiments, the size of the second taper angle 620 is about −1°.

The narrow end 612 of the first tapered portion 608 can be at approximately the same axial position as the narrow end 622 of the second tapered portion 618, although it is also contemplated that they also could be axially spaced from one another. The second tapered portion 618 and the first tapered portion 608 may be a single, continuous structure or may be distinct components integrally connected. The juncture where of the narrow ends 612 and 622 meet defines an inflection location 625 of the waisted portion 630 of the cannula 600. In this exemplary embodiment, the remote center of the cannula 600 is disposed at the inflection location 625.

As further depicted in FIG. 6B, a third taper 626 defines the lateral (e.g., radial) outer limits of a third tapered portion 628 (also called third tapered region 628) of cannula 600. Third tapered portion 628 includes a distal end of the cannula, with proximal and distal directions labeled on FIG. 6B. The third taper 626 has a third taper angle 640 measured relative to the longitudinal axis 604 of the cannula 600. Third tapered portion 628 has a third tapered portion narrow end 632 and a third tapered portion wide end 634.

Various third taper angle 640 sizes are contemplated. For example, the size of the third taper angle 640 may range from about 1° to about 5°. The longitudinal length of the third tapered region 628 (i.e., the length of the third tapered region 628 extending from the third tapered portion narrow end 632 and a third tapered portion wide end 634) may range considered when sizing the third taper angle 640. For example, when the longitudinal length of the third tapered region 628 is relatively large (e.g., about 20 to about 50 millimeters in length), the size of the third taper angle 640 may range from about 1° to about 2°. Alternatively, for example, when the longitudinal length of the third tapered region 628 is relatively small (e.g., about 5 to about 20 millimeters in length), the size of the third taper angle 640 may be from about 2° to about 3°. In some embodiments, the size of the third taper angle 640 is about 2°.

In various embodiments, the magnitude of the size of the first taper angle 610 and the magnitude the size of the second taper angle 620 may range about the same. Further, in some embodiments, the magnitude of the size of the third taper angle 640 may be relatively larger than the magnitude of the size of the first taper angle 610 and/or the magnitude the size of the second taper angle 620. Thus, in various exemplary embodiments, the size of the first taper angle 610 ranges from about 1° to about 2°, the size of the second taper angle 620 ranges from about −1° to about −2°, and the size of the third taper angle 640 ranges from about 2° to about 3°. Accordingly, in an exemplary embodiment, the size of the first taper angle 310 is about 1°, the size of the second taper angle 620 is about −1°, and the size of the third taper angle 340 is about 2°.

The wide end 624 of the second tapered portion 618 may be collocated or slightly axially spaced from the wide end 634 of the third tapered portion 628. The second tapered portion 618 and the third tapered portion 628 may be a single, continuous structure or may be distinct components that are integrally connected.

In the exemplary embodiment of FIGS. 6A and 6B, the outer wall surface 602 is smooth and free of ribs. Referring again to FIG. 6B, within the first tapered portion 608, the outer lateral wall surface 602 is incident upon and defines the first taper 606. Likewise, within the second tapered portion 618, the outer lateral wall surface 602 is incident upon and defines the second taper 616, and the outer lateral wall surface 602 within the third tapered portion 628 is incident upon and defines the third taper 626. Providing an outer lateral wall surface 602 that defines the tapers 606, 616, and 626, as exemplified by cannula 600, can be achieved by varying the thickness of the cannula wall, i.e., by varying the lateral distance between the outer lateral wall surface and the inner lateral wall surface, or by maintaining a uniform wall thickness, and having the inner and outer wall surfaces follow the same tapering and extend parallel to each other along the cannula.

Although not shown in cannula 600 of FIGS. 6A-6B, a smooth cannula can include indicia, such as body wall targets formed from different coloring or texturing or other indicia, as described and shown on cannulas 200, 300 in FIGS. 2B and 3B-3C, respectively. For example, cannula 600 can include an upper body wall target, a lower body wall target, and a central body wall target, as described above but not depicted in FIGS. 6A and 6B. The remote center and inflection location 625 of the cannula 600 may be at the center of a central body wall target (not shown). Alternatively, it is also contemplated that the center of the central body wall target of a smooth cannula can be offset from the remote center and/or inflection location of the cannula.

According to various other exemplary embodiments (not shown), a portion of the cannula proximally adjacent to the inflection location need not be a tapered portion such as first tapered portions 206, 306, 608, but rather outer lateral dimensions of the portion proximally adjacent from the inflection location could extend generally parallel to the longitudinal axis of the cannula. In other words, it is contemplated that the first taper angle 210, 310, 610 as described above is 0°.

In yet other various exemplary embodiments (not shown), a distal end portion of the cannulas need not include a tapered portion such as third tapered portions 228, 328, 628, but rather outer lateral dimensions could extend generally parallel to the longitudinal axis of the cannula. In other words, it is contemplated that a third taper angle 240, 340, 640 as described above is 0°.

Additionally, in various exemplary embodiments (not shown), a distal end portion of a cannula is a distally flared third tapered portion. In other words, it is contemplated that a third taper angle 240, 340, 640, as described above, may have a size ranging from −1° to about −5°. For example, third taper angle 240, 340, 640 may be substantially the same size as second taper angle 220, 320, 620, such that the cannula tapers consistently along the longitudinal length throughout the second tapered portion 218, 318, 618 and third tapered portions 228, 328, 628. In particular, the size of third taper angle 240, 340, 640 may be about −1° and the size of second taper angle 220, 320, 620 may be about −1°. In another exemplary embodiment, the magnitude of the third taper angle 240, 340, 640 of a distally flared third tapered portion may be greater than the magnitude of the second taper angle 220, 320, 620. For example, the size of third taper angle 240, 340, 640 may be about −2° and the size of second taper angle 220, 320, 620 may be about −1°.

The cannulas of the present disclosure have various exemplary applications. For example, the cannulas of the present disclosure can be used in surgical procedure, such as a minimally invasive surgical procedure. Contemplated surgical procedures include diagnostic surgical procedures and therapeutic surgical procedures.

Although the cannulas have been described herein with reference to teleoperated surgical systems, the present disclosure contemplates non-teleoperated surgical instruments, such as, for example, manually operated surgical instruments (e.g., hand held surgical instruments), which may be used with the various exemplary embodiments described herein.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the scope of the present disclosure and following claims.

The nature of information depicted in the figures and described herein is exemplary. Those persons having skilled in the art would appreciate modifications to the cannulas can be made, such as for example, modifications to structure, dimensions, materials, and methodologies may be made without departing from the scope of the present disclosure.

It is to be understood that the particular examples and embodiments set forth herein are non-limiting, and modifications to structure, dimensions, materials, and methodologies may be made without departing from the scope of the present disclosure and claims including equivalents.

Other embodiments in accordance with the present disclosure will be apparent to those skilled in the art from consideration of the specification and practice of the invention disclosed herein. It is intended that the specification and examples be considered as exemplary only, with being entitled to their full breadth of scope, including equivalents.

What is claimed is:

1. A cannula comprising:
    a cannula bowl having an opening to receive an instrument configured to be advanced through the cannula; and
    a cannula tube extending distally from the cannula bowl, the cannula tube comprising:
        a proximal end opening;
        a distal end opening disposed at an opposite end of the cannula from the proximal end opening;
        a lateral wall defining a passage extending from the proximal end opening to the distal end opening, the lateral wall comprising a waisted portion, a first region proximal of the waisted portion along a length of the cannula tube, and a second region distal of the waisted portion along the length of the cannula tube, the waisted portion having an outer dimension smaller than an outer dimension of the first region and smaller than an outer dimension of the second region; and
        a series of axially-spaced ribs each radially extending from an outer surface of the lateral wall at least along the waisted portion.

2. The cannula of claim 1, wherein the waisted portion is located along a length of the cannula configured to be surrounded by a body wall in an inserted position of the cannula through an opening in the body wall.

3. The cannula of claim 1, wherein the cannula tube further comprises:
    a proximal region extending proximally from the waisted portion; and
    a distal region extending distally from the waisted portion;
    wherein the proximal and distal regions have larger outer lateral dimensions than a lateral dimension of at least part of the waisted portion.

4. The cannula of claim 1, wherein the waisted portion comprises:
    a first tapered portion extending between a first tapered portion narrow end and a first tapered portion wide end; and
    a second tapered portion extending between a second tapered portion narrow end and a second tapered portion wide end;
    wherein a discontinuity of the shape of the waisted portion is defined where the first tapered portion narrow end and the second tapered portion narrow end meet.

5. The cannula of claim 4, wherein a thickness of the lateral wall is larger at the first and second tapered portion wide ends than a thickness of the lateral wall at the first and second tapered portion narrow ends.

6. The cannula of claim 4, wherein:
    a radial outer limit of each rib within the first tapered portion is incident upon a first imaginary surface defining a first taper of the first tapered portion; and
    a radial outer limit of each rib within the second tapered portion is incident upon a second imaginary surface defining a second taper of the second tapered portion.

7. The cannula of claim 6, wherein the lateral wall has a uniform thickness over a length of the waisted portion of the cannula tube.

8. The cannula of claim 6, wherein, along the length of the lateral wall within the waisted portion, the outer surface of the first tapered portion is parallel to the first imaginary surface defining the first taper and the outer surface of the second tapered portion is parallel to the second imaginary surface defining the second taper such that a thickness of the lateral wall is larger at the first and second tapered portion wide ends than a thickness of the lateral wall at the first and second tapered portion narrow ends.

9. The cannula of claim 6, wherein a profile of each rib of the series of ribs along a longitudinal cross section of the cannula tube is generally triangular in shape.

10. The cannula of claim 9, wherein each rib of the series of ribs along the longitudinal cross section of the cannula tube terminates in an apex disposed radially outwardly from the lateral wall, an apex angle of the apex of each rib being the same.

11. The cannula of claim 9, wherein each rib of the series of ribs along the longitudinal cross section of the cannula tube terminates in an apex disposed radially outwardly from the lateral wall, an apex angle of at least some of the ribs of the series of ribs along the longitudinal cross section of the cannula tube varying from each other.

12. The cannula of claim 4, wherein:
    the first tapered portion has a first taper angle from 1 degree to 5 degrees relative to a longitudinal axis of the cannula tube; and the second tapered portion has a second taper angle from −1 degree to −5 degrees relative to the longitudinal axis of the cannula tube.

13. The cannula of claim 4, wherein:
the cannula tube further comprises a third tapered portion including a third tapered portion narrow end and third tapered portion wide end; and
the third tapered portion extends distally from the second tapered portion.

14. The cannula of claim 1, wherein:
the waisted portion defines an inflection;
ribs proximal to the inflection flare outwardly in one of a proximal-to-distal direction and a distal-to-proximal direction; and
ribs distal to the inflection flare outwardly in the other of the proximal-to-distal direction and the distal-to-proximal direction.

15. The cannula of claim 1, wherein:
ribs of the series of axially-spaced ribs are configured to be incident along imaginary surfaces defining proximally and distally extending tapers;
the proximally extending taper extends proximally from an inflection of the waisted portion and tapers in a direction from proximal-to-distal; and
the distally extending taper extends distally from the inflection and tapers in a direction from distal-to-proximal.

16. The cannula of claim 1, wherein a thickness of the lateral wall along at least the waisted portion varies.

17. The cannula of claim 1, wherein a thickness of the lateral wall along at least the waisted portion is uniform.

18. A method of making a cannula, the method comprising:
configuring outer dimensions of the cannula to comprise a cannula bowl and a cannula tube extending distally from the cannula bowl; the cannula bowl comprising an opening to receive an instrument configured to be advanced through the cannula; the cannula tube comprising a proximal end opening, a distal end opening at an opposite end of the cannula tube from the proximal end opening, a lateral wall defining a passage extending from the proximal end opening to the distal end opening, and a series of axially-spaced ribs; the lateral wall comprising an outer surface, a waisted portion, a first region proximal of the waisted portion along a length of the cannula tube, and a second region distal of the waisted portion along the length of the cannula tube; the waisted portion comprising an outer dimension smaller than an outer dimension of the first region and smaller than an outer dimension of the second region; and the series of axially-spaced ribs each radially extending from the outer surface of the lateral wall of the cannula at least along the waisted portion.

19. The method of claim 18, wherein: a first tapered portion and a second tapered portion;
the first tapered portion comprising a first tapered portion narrow end and first tapered portion wide end; and
the second tapered portion comprising a second tapered portion narrow end and second tapered portion wide end; and
the first tapered portion narrow end and the second tapered portion narrow end meet at a juncture to define a discontinuity of the shape of the waisted portion.

* * * * *